(12) United States Patent
Timmann et al.

(10) Patent No.: US 8,672,538 B2
(45) Date of Patent: Mar. 18, 2014

(54) TEMPERING APPARATUS WITH TESTING DEVICE AND METHOD FOR TESTING A TEMPERING APPARATUS

(71) Applicant: Eppendorf AG, Hamburg (DE)

(72) Inventors: Lutz Timmann, Fuhlendorf (DE); Vinh Duong, Norderstedt (DE); Stefan Roth, Hamburg (DE); Thomas Uschkureit, Henstedt-Ulzburg (DE); Jurgen Koeppel, Großhansdorf (DE); Thomas Buck, Hamburg (DE); Michael Wild, Henstedt-Ulzburg (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 13/657,599

(22) Filed: Oct. 22, 2012

(65) Prior Publication Data

US 2013/0114639 A1  May 9, 2013

Related U.S. Application Data

(63) Continuation of application No. 12/534,619, filed on Aug. 3, 2009, now Pat. No. 8,322,918.

(60) Provisional application No. 61/085,599, filed on Aug. 1, 2008.

(51) Int. Cl.
*G01N 25/00*  (2006.01)
(52) U.S. Cl.
USPC ......................................... 374/45

(58) Field of Classification Search
USPC ........... 73/149, 308, 717, 724, 304 R; 374/45
See application file for complete search history.

(56) References Cited

U.S. PATENT DOCUMENTS

| 6,767,512 B1* | 7/2004 | Lurz et al. ..................... 422/552 |
| 2006/0105433 A1* | 5/2006 | Bickmore et al. ........... 435/91.2 |
| 2009/0203082 A1* | 8/2009 | Schlaubitz et al. .......... 435/91.2 |
| 2010/0116896 A1* | 5/2010 | Goemann-Thoss et al. 236/91 R |
| 2011/0151519 A1* | 6/2011 | Tasch et al. .................. 435/91.2 |

* cited by examiner

*Primary Examiner* — Lisa Caputo
*Assistant Examiner* — Jamel Williams
(74) *Attorney, Agent, or Firm* — Todd Lorenz; Arnold & Porter LLP

(57) ABSTRACT

The invention relates to a tempering apparatus for tempering a sample comprising: at least one tempering block configured for receiving at least one sample, at least one tempering device arranged for tempering the tempering block, at least one temperature measurement device assigned to the tempering device, at least one control loop to which the tempering device and temperature measurement device are assigned to, at least one control device configured for control of the tempering of the tempering block, wherein the tempering apparatus comprises at least two temperature measurement devices assigned to the control loop, and that to the tempering apparatus a testing device for performing a test method is assigned to, wherein the testing device comprises a signal-connection to at least one of the at least two temperature measurement devices, such that at least one testing quantity of the tempering apparatus is detectable, which characterizes the operational status of the tempering apparatus.

5 Claims, 11 Drawing Sheets

Figure 1:
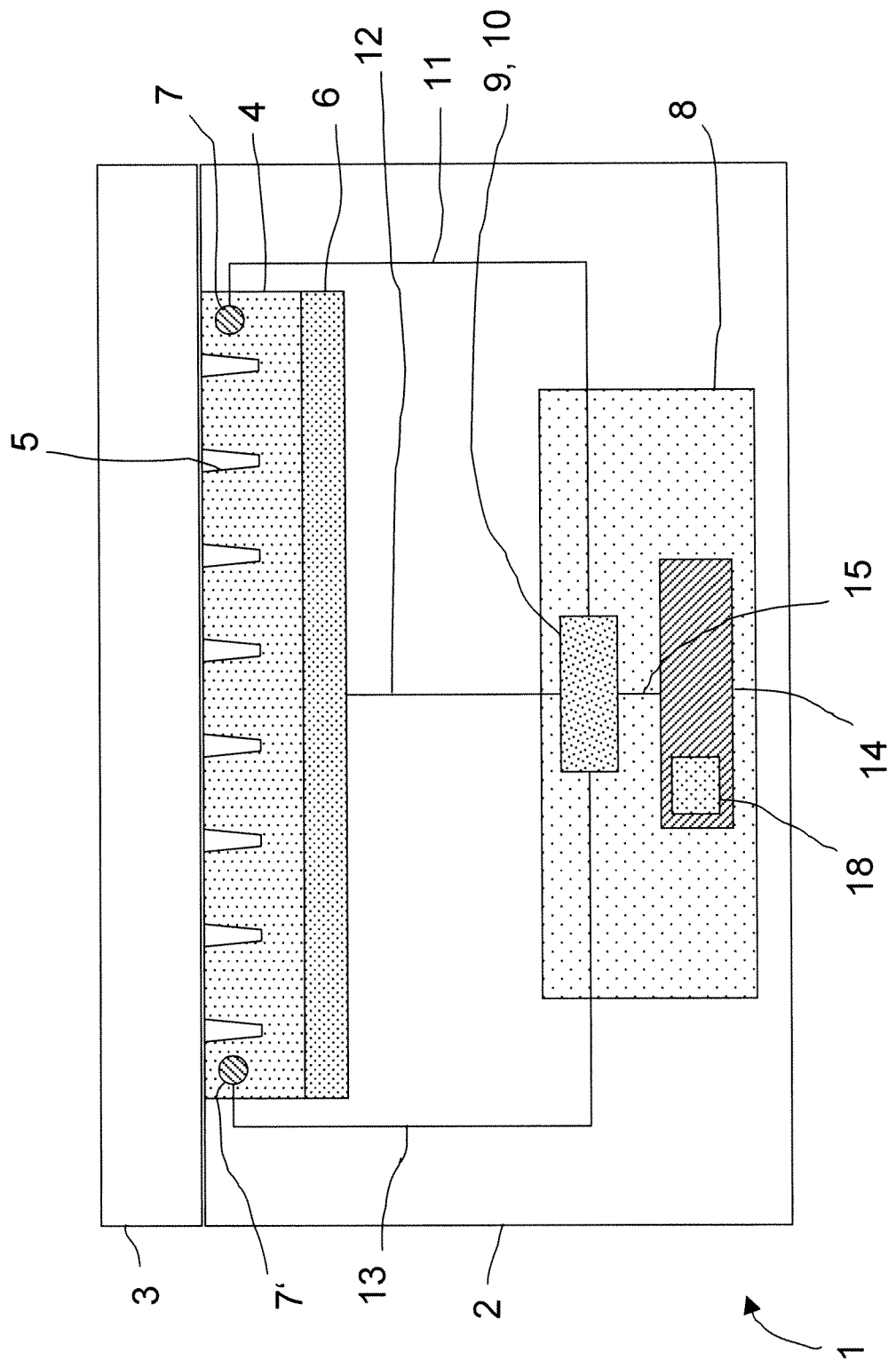

TEMPERING APPARATUS WITH TESTING DEVICE AND METHOD FOR TESTING A TEMPERING APPARATUS

The invention relates to a tempering apparatus for the tempering of at least one sample with testing device and a method for testing a tempering apparatus.

Tempering apparatus are being used for example as thermostats, thermomixers or thermocyclers in examination-, research- or fabrication laboratories, for example for bringing a liquid sample to a desired temperature. The precise adjustment of predetermined temperatures in samples is in particular important for chemical reactions, whose successful execution depends in a critical way on the compliance with at least one certain temperature or with a temporarily changing temperature profile. An example for such a chemical reaction is the polymerase chain reaction (PCR). By such a PCR reaction DNA-sequences can be efficiently amplified, for which reason said method is applied with increasing importance, for example in pharmacy, medicine, research or forensic science.

The precise maintaining of certain temperature values, to which a sample is cyclically subjected during a PCR tempering program, is critical for the successful execution of a PCR, in particular of a quantitative PCR. In a PCR, the cycle periods of denaturation, primer hybridization and elongation are controlled by different precisely defined temperature levels. The quality of the PCR critically depends on the capability of the components of the tempering apparatus being used and thus on its operating condition. In particular if, for example, for medical or legal medical reasons high demands are made on the reliability and reproducibility of a PCR, the control of the operating condition of the tempering apparatus being used becomes important.

It is convenient for tempering apparatus with electrically adjustable tempering devices as, for example, Peltier elements, to set a desired temperature by means of a control loop, whose actuating member is the Peltier element and whose measuring member comprises a temperature sensor. In said control loop the actuating member is operated with the objective of bringing the temperature measured by the measuring member in accordance with a set temperature. However, failures of such an apparatus can occur, which compromise its capability, but which do thereby not impede the function of the apparatus during the proceeding operation in a way such that it is directly recognizable by the user. Such failures can be, for example, performance variations of the tempering device over its age or the drift of sensors. In particular for the examination of the operability of the temperature sensors it is known to make use of external thermometer and calibration sets which measure a temperature at the apparatus. However, such an examination requires a relatively high effort in hardware, manpower and expenditure of time.

It is object of the present invention to provide an improved tempering apparatus, which, in particular, operates reliably and at which, in particular, possible operation failures are easily detectable, and who provide an improved method for testing the function of a tempering apparatus.

Said object is made by the tempering apparatus according to claim 1 and the method according to claim 6 of the present invention. Preferred embodiments of the invention are subject of the sub-claims.

The tempering apparatus according to the invention for the execution of a tempering program with at least one sample, in particular a PCR sample, comprises at least one tempering block, which is configured for the reception of at least one sample, at least one tempering device, which is arranged for the tempering of said at least one tempering block, at least one temperature measurement device, which is assigned to said tempering device, at least one control loop for controlling a temperature, to which at least one tempering device and at least one temperature measurement device, which is assigned to said at least one tempering device, are assigned, at least one control device, which is configured for the control of the tempering of the at least one tempering block, wherein the tempering apparatus comprises at least two temperature measurement devices, which are assigned to at least one control loop, and wherein at least one test device for the execution of a test method is assigned to the tempering apparatus, wherein said test device comprises a signal-connection with at least one of said at least two temperature measurement devices, such that by means of said signal-connection at least one test quantity of the tempering apparatus is determinable, which characterizes the operating condition of the tempering apparatus.

Such a tempering apparatus preferably is a thermomixer for the simultaneous mixing and tempering of at least one sample, or is a thermostat, which is configured for the execution of a tempering program of at least one sample. The tempering program thereby comprises at least the step of tempering at least one sample to a least one target temperature. This is preferably carried out by the manual or automatic setting of at least one set temperature as a target temperature at said at least one control loop.

Further, said tempering apparatus preferably comprises the function of a thermocycler or is configured as a thermocycler. The latter is preferably appropriate for the execution of a PCR reaction within at least one PCR sample. Said tempering apparatus is preferably a thermocycler. The tempering program thereby preferably comprises at least the tempering steps of a PCR cycle during whom the PCR sample is tempered in a temporal sequence to at least two or three temperatures. By means of a single tempering program a PCR reaction within at least one PCR sample is preferably executed by repeating the tempering steps of a PCR cycle multiple times, in particular 10 to 70 times. It can be desirable to find out the critical temperature levels of a PCR by applying a spatial temperature gradient, i.e. a spatially changing temperature profile with at least two different temperatures. For said purpose, a temperature gradient is generated in the tempering block along a distance, along which also a plurality of PCR samples are arranged to, which therefore are exposed to different temperatures, which lead to PCR results of differing quality. The temperature gradient can, for example, be generated by at least two tempering devices, which are arranged below the tempering block, as it is described in the WO 98/020975 A1. This offers the advantage that the tempering block can also be brought to a uniform temperature by generating the same temperature by means of said at least two tempering devices. Moreover, a temperature gradient can be used to hold the samples, which are provided in the receptacles of a tempering block at different temperatures which is, for example, reasonable if the samples are group-wise running through different reaction phases. Thus, a temperature gradient can have continuous temperature changes or can be step-shaped. Alternatively, the generation of a temperature gradient can be provided by other arrangements, wherein at least two different temperatures are applied to the tempering block. The tempering apparatus can comprise one or more tempering devices, possibly even in each case one for a low number of samples, for example one for each sample or one for two samples.

Other possible tempering apparatus are work stations and other apparatus, which can apply a tempering program simultaneously to one or more samples.

The tempering block is preferably configured according to the tempering block described in WO 98/020975 A1. A tempering block here refers to a component whose configuration allows to temper at least one sample, which is arranged at or in the tempering block. Preferably, the tempering block comprises at least one integrally formed, preferably substantially cuboidal-shaped component, made from a well heat-conducting material, in particular metal, for example aluminium or silver. It is moreover possible and preferred that said tempering block is divided into at least two, in particular three, four, five, six or more integrally formed sections made from a well heat-conducting material, which are separated by a worse heat-conducting medium or material. Within said component or within each of said sections, preferably at their upper surface, at least one receptacle for a sample or a sample vessel is arranged. Said receptacle is preferably arranged as a recess at the surface of said section or said tempering block. Said receptacle or the recess are preferably configured for a large-area contacting of a sample vessel, for achieving an efficient heat transfer from the tempering block to the sample vessel and to the sample contained therein. Whenever a tempering block is mentioned in the following, it also refers to a tempering block section, if not described otherwise or if not reasonable.

Preferably, said tempering block is configured for the reception of a plurality of samples or sample vessels. Preferably, said tempering block is configured for the reception of at least one sample plate, at which a plurality of sample vessels are arranged side by side. Such a sample plate is preferably a microtiter plate or a PCR plate. Herein, the number of sample vessels is, in particular, respectively preferred 2, 4, 8, 12, 16, 24, 48, 96, 384 or 1536.

The tempering device is preferably assigned to a control loop and is preferably an electrically controllable device. The "assignment" of a component part, for example that of a tempering device or a tempering apparatus to a control loop, involves in the scope of the present invention preferably the functional assignment, according to which the component part takes over a function of the control loop and for example contributes as a part of the control loop to the regulation of the temperature of at least one section of the tempering block, and involves that, for example, a tempering device serves as an actuating member of the control loop. Preferably, said tempering device comprises a Peltier element. However, another type of tempering device can be provided, for example comprising an electrically resistive element. For the tempering of said at least one tempering block the tempering device is preferably arranged under its underside. The tempering device preferably contacts the tempering block in a large-area manner, wherein said tempering device provides a dimensioning, which allows the tempering of a plurality of samples by means of a single tempering device. To achieve this, the tempering device is preferably arranged below a plurality of receptacles for samples or sample vessels, which are arranged above said tempering device in the tempering block.

To each tempering device at least one temperature measurement device is assigned. Therefore, said temperature measurement device is appropriate to measure the temperature, which is adjusted to said tempering block by means of said tempering device. However, the measured temperature can in a lower extent also be influenced by such tempering devices to which the temperature measurement device is not assigned to. The assignment of a temperature measurement device to a tempering device, which is assigned functionally to a control loop, preferably involves that also said temperature measurement device takes over a function of the control loop and, for example, contributes as a part of the control loop to the regulation of the temperature of at least one section of the tempering block and that, in particular, said temperature measurement device serves as a measuring member of the control loop.

For the detection of the temperature of the tempering block said temperature measurement device is preferably arranged at said tempering block. The temperature measurement device is preferably arranged in a distance from said tempering device. Said distance is preferably such that it corresponds to a distance between the tempering device and a receptacle of the tempering block. This offers the advantage that by means of said temperature measurement device the temperature can be measured, which is pending at said receptacle and which is thus applied to said sample vessel. However, the distance can also be chosen differently. Further, it is preferred that at least one temperature measurement device is arranged in a boundary area of a tempering block. Preferably, at least two tempering devices are arranged at the tempering block in a maximum possible distance, wherein the maximum distance can, for example, be determined by the length or the width of the tempering block (-section) and/or the dimensions and/or other predetermined parameters, for example the position of arrangement of the temperature measurement device at the upper side or the border side of the tempering block. The border side of the tempering block can provide a different temperature than a central area of the tempering block due to the environmental temperature or due to the convective heat transport of environmental air. Therefore, the measurement at the border side of the tempering block is in particular of advantage to achieve temperature control there. Further, the measurement in the border area can be of advantage to generate and control a temperature gradient within the tempering block, which extends from one end, i.e. border area of the tempering block to the other end. The measuring at the border area can moreover also be of advantage, because the heat flow within the tempering block will not be hindered by the temperature measurement device. A temperature measurement device is preferably attached to the tempering block, for example adhered to, or preferably at least in part incorporated into a recess or opening of the tempering block. The temperature measurement device is preferably an electronic component and can, for example, comprise a semiconductor temperature sensor, a thermoelement or a pyrometer.

Preferably, at least one temperature measurement device is arranged in a low distance or in direct contact with at least one tempering device. Said low distance is preferably lower than 0.5 times, 0.25 times or 0.1 times a thickness of the tempering block. Said temperature measurement device is preferably functionally assigned to a control loop or preferably not functionally assigned to a control loop. The advantage of a low distance is that a shorter distance for heat transfer between the temperature measurement device and the tempering device is generated, whereby a change of the temperature of a tempering device can be detected faster than in the case of a larger distance between the temperature measurement device and the tempering device. This is, in particular, of advantage to test the operability of the tempering device, in particular by means of the test method according to the invention. A shorter overall duration of the test method can effect that it can be tested more frequently, whereby the reliability of the tempering apparatus can be monitored in a better way.

The tempering apparatus further preferably provides at least one temperature measurement device, which is configured as safety sensor. Such a safety sensor is preferably signal-connected to the control device and configured to detect a predetermined extreme temperature in the tempering apparatus, whose detection preferably leads to a safety procedure of the tempering apparatus, for example to the output of a warning signal or to the shut-down of the tempering apparatus. A safety sensor is preferably arranged for the safeguarding of temperature of the tempering block in the vicinity of a temperature measurement device, which is assigned to a control loop. The safety sensor is not assigned to a control loop. In this way, a malfunctioning control loop less probably also involves also the malfunction of the safety sensor. Said "vicinity" of a temperature measurement device is preferably an area, which lies in a distance to said temperature measurement device, wherein the distance is preferably lower than the maximum distance of two temperature measurement devices of the tempering apparatus, which are assigned to at least one control loop, is preferably lower than the minimum distance of two temperature measurement devices of the tempering apparatus, which are assigned to a control loop, is preferably lower than a width of the tempering device, is preferably lower than the height of a tempering block, which can, for example, 3 cm, and is preferably lower than 1 cm. A safety sensor can, in particular, be arranged in direct or indirect contact with another temperature measurement device, in particular without being separated from a section of the tempering block or from the environmental air.

A control loop is preferably assigned to a control device, which is configured for the control of the tempering of the at least one tempering block. However, it is also possible and preferred, that a tempering device and at least one temperature measurement device, which is assigned to said one tempering device, are provided, which are only at least temporarily assigned to no control loop by having them excluded or being switched off from their control functions (actuating member, measuring member) by way of program control. Such a control of said tempering device and said temperature measurement device offers a further increased flexibility for the configuration of a test method. Further, the independency of a component, in particular of a temperature measurement device, on the control loop can lead to an increase of the reliability of testing said control loop by means of said component. During the regulation of the temperature in a tempering block by means of said control loop, said control device is signal-connected to said at least one control loop and to at least one temperature measurement device, which is assigned to said at least one control loop.

Within the scope of the invention two devices are considered to be signal-connected, between which signals can be exchanged. Said signals are thereby preferably bound to a medium, as for example to an electrical conductor or semiconductor. It is possible and preferred, that said signals, which are exchanged between said two signal-connected devices, are exchanged via a mediation device, by, for example, letting a first device sending a signal to the mediation device, where the signal is buffered and is optionally also modified, before a second device accesses the buffered signal, to receive it. For example, said temperature measurement device of a control loop can supply a measuring signal, which is buffered by a memory device of the control loop such that the testing device can access said memory device for receiving said measuring signal. In this example the testing device is signal-connected to the temperature measurement device. However, it is also possible that said signals are transferred without being bound to a conducting material, i.e. being transferred to the space, as for example possible for electromagnetic rays (for example radio waves or infrared light) as well as by sound waves through a space, which is at least filled by gas. Herein, by the term "signal-connected" uni- as well as bidirectional transmission lines are covered.

To each control loop preferably at least two temperature measurement devices and at least one tempering device, which is assigned to said temperature measurement devices, are assigned. Conventional tempering apparatus, in particular thermocycler, commonly possess more than one tempering device per control loop and temperature sensor. This way, the malfunction of a tempering device can generally not be recognized, because the deviations in the performance do not mandatory lead to a failing temperature at the temperature measurement device, which is provided for measuring the temperature of the section in the tempering block, which is tempered by said tempering device. Nevertheless, said deviations in performance lead to an inhomogeneous distribution of temperatures at said sample block, because different power rates are introduced at different locations via the single tempering devices. Moreover, incorrect sensor values, for example caused by changes of the contacting or by drift, are not recognized. For the improvement of said situation, at least one temperature measurement device and, in particular, a second temperature measurement device are assigned to each tempering device. This way, a number of test method can be executed in a flexible way, in particular by means of the testing device. By the comparison of test quantities, in particular the comparison of temperature measuring values and of temperature changing velocities, with reference values or in particular with other measured testing quantities, the operating condition of a network of components, of single components of the tempering apparatus or of the overall tempering apparatus can be determined. The testing device is preferably signal-connected to at least one, in particular to each control loop and preferably signal-connected to at least one, in particular each temperature measurement device, which is assigned to said control loop.

Especially preferred, the tempering apparatus comprises at least one control loop, to which at least two tempering devices and at least two temperature measurement devices are assigned to, wherein at least one temperature measurement device is assigned to each tempering device. In particular, the tempering apparatus comprises preferably a number of control loops, to which respectively two tempering devices and two temperature measurement devices are assigned to. Said number is preferably 2, 3, 4, 5, 6, 7, 8 or higher.

Preferably, exactly one temperature measurement device is assigned to each tempering device and preferably exactly said tempering device is assigned to said temperature measurement device. It is further preferred, that at least two temperature measurement devices, in particular exactly two, are assigned to one tempering device. This way, the testing of the tempering apparatus can be further improved and be rendered in particular more reliable and more precise, and this way the tempering apparatus can be improved. Further, preferably exactly two temperature measurement devices are assigned to each tempering device and exactly said tempering devices are assigned to said two temperature measurement devices.

The tempering apparatus preferably comprises at least two tempering devices, which are arranged for the tempering of said at least one tempering block, at least two temperature measurement devices wherein at least one temperature measurement device is assigned to each tempering device, and at least one first control loop and one second control loop. The use of at least two control loops may, in particular, allow to apply at least two different temperatures to said at least one tempering block. Preferably, said at least two tempering devices are arranged for the generation of a temperature gradient, that is a temperature profile with at least two different temperature values, which extends within said at least one tempering block. It shall be understood, that by means of two different tempering devices also a single temperature can be applied to at least one tempering block. Preferably, said testing device comprises a signal-connection to each tempering device and to each temperature measurement device of said first and second control loop, wherein by means of the testing device a first testing quantity is determinable, which is assigned to said first control loop, and wherein a second testing quantity is determinable, which is assigned to said second control loop. Preferably, said testing device comprises a means for the comparison of said two testing quantities or for the comparison of said testing quantity with another reference quantity. The reference quantity can be a stored quantity or a measured quantity, in particular a testing quantity.

Said control device preferably comprises electrical circuits, which are configured for the control of a tempering of the at least one tempering block. Further, said control device preferably comprises means for the digital data processing. The control loop preferably comprises a processing unit, which can be a CPU, a microprocessor or a microcontroller.

Preferably, said control device comprises circuits, which are configured for processing a program code, in particular for the processing of programs for the temperature regulation or programs for executing a test method, in particular the test method according to the invention. Further, the control device preferably comprises at least one memory unit for the storage of data or signals, which preferably is also removable from the control device. Said memory unit preferably comprises data storage for the temporary storage of data, for example RAM and/or data storage for the permanent storage of date, for example hard disc or flash memory. Further, said control device preferably comprises at least one interface for establishing a signal-connection between said control device and another device, for example a testing device in an external embodiment, to an external data storage, to a control apparatus, to an external PC, to a control panel or to another device. Further, said control device preferably comprises circuits, for example power electronics, for a control of components for the energy supply, which can serve, for example, for the power supply of said control device, said at least one tempering device are said at least one temperature measurement device. For the regulation of a temperature within said tempering block by means of said control loop, said control device is signal-connected to said at least one control loop and to at least one temperature measurement device, which is assigned to said at least one control loop.

The testing device is preferably arranged in the tempering apparatus and is preferably constructionally integrated in the control device. However, it is also possible and preferred, that the testing device is an at least substantially separate component. The testing device preferably comprises electrical circuits, which are appropriate for processing signals, which are required for the execution of the testing method. Preferably, the electrical circuits of the testing device are at least substantially separated from the circuits of the control device, forasmuch as no signal lines have to be used together. In that case, the circuits of the testing device are preferably arranged in a spatial offset to the circuits of the control device. This offers the advantage that their arrangement is more flexible and can, for example, be configured for minimizing detrimental thermal or corrosive effects, for example by encapsulation. In this way, the reliability of the testing device and thus of the tempering apparatus can be improved. The testing device preferably comprises at least one signal-connection to at least one tempering device, in a way that it puts out signals, which influence the operating condition of the tempering device. The testing device further preferably comprises at least one signal-connection to at least one control loop, by being capable of exchanging signals with at least one component of the control loop, for example of its actuating member, which controls the supplying power to the tempering device, or its measuring member (sensor). Further, the testing device is preferably signal-connected to at least one power control device, which controls and measures the power, which is put in to a tempering element.

It is further possible and preferred, that the testing device, which is assigned to said tempering apparatus for the execution of a testing method, is arranged externally outside the tempering apparatus, wherein said testing device comprises a signal-connection to said at least one temperature measurement device. Said signal-connection at such a testing device in external embodiment preferably takes place via an interface, which is provided at said tempering apparatus, in particular at said control device. This way it is possible that a central control of the testing method takes place, for example by means of a control center or an laboratory information management system (LIMS), which, in particular, can control a plurality of tempering apparatus.

The execution of a testing method by means of an external testing device preferably takes place without a manual intervention of a user to said tempering apparatus and preferably takes place automatically. An external testing device can, in particular, comprise a control device, which can comprise a microcontroller, an input device, for example a keyboard, an input panel and, an output device, for example a display. Preferably, an external testing device is a PCR workstation. In particular, an external testing device can be the component of an external control center or control device, for example a PC or workstation, which administrate further tasks for the control of further devices, for example in an automatic measuring system or by means of a LIMS.

Preferably, said tempering apparatus and, in particular, said control device are configured for the remote control of at least one function of the tempering apparatus or of a component of said tempering apparatus. Preferably, said tempering apparatus, in particular said control device, is configured for the remote access to at least one component of said tempering apparatus. Preferably, said tempering apparatus, in particular said control device, is configured for the remote access of an external testing device, which is assigned to said tempering apparatus for the execution of a testing method. By having also said external testing device comprising a signal-connection to a control loop and to a temperature measurement device, the execution of the testing method can take place remote controlled. It can, for example, be provided that the testing method is executed remote by a service professional or is executed automatically, to determine the operating status of said tempering apparatus and are to gain operational data, in particular said at least one testing quantity of the tempering apparatus, for the monitoring of functions or the remote diagnosis of the operating condition of said tempering apparatus. In particular, it can be provided that said external testing device is part of a diagnosis and maintenance apparatus, which a service professional connects to said tempering apparatus for the execution of a testing device. However, it is also possible and preferred that said external testing device stands in signal-connection to said tempering apparatus over larger distances. Preferably, said tempering apparatus, in particular said control device, is configured for the signal-connection via a network- or internet-connection or similar long distance lines. In this case, an external testing device can stand in signal-connection to said tempering apparatus via said long distance line and start a testing method and execute it. Since a signal-connection can also take place wireless and thus also over larger distances and through walls and obstacles, for example by an electromagnetic signal transfer in the GHz range, a testing of a testing quantity of said tempering apparatus can be configured even more flexible.

The tempering apparatus further preferably comprises a starting device, which is appropriate for the manual and/or automatically starting of a testing method, which is executed by said testing device. The starting device is preferably structurally integrated into the testing device or the control device, but can also be realized separately. The starting device preferably comprises circuits, which are appropriate for processing starting signals and/or in particular for the processing of a starting program code. The starting device is preferably configured for a manual starting, in particular, for a direct or a time-delayed starting of a testing method of the testing device of said tempering apparatus. The starting device can comprise at least one input device, for example an actuation element as perhaps are a knob or a sensor field on a control panel of the tempering apparatus, which is signal-connected to said testing device and configured at least for effecting a starting signal by the user. Further, the starting device is preferably configured for the automatic starting of a testing method of the testing device of said tempering apparatus. The automatic starting also includes a semi-automatic starting. For performing a semi-automatic starting, the starting device is preferably configured for letting the actuation of an input device by the user lead to the automatic, in particular program controlled starting of the testing method, for example by means of a starting program. In particular, the starting device is equipped with at least one starting program, which the user can choose by means of said input device, to determine the starting of at least one testing device.

The starting device, in particular a starting program, is preferably configured in a way that the starting of a testing method takes place before or after each measurement on said at least one sample, which is performed by means of said tempering apparatus, and takes place, in particular, for each execution of a tempering program. The starting device, in particular a starting program, is further preferably configured the way that starting the testing method takes place in regular periods automatically after each $n^{th}$ ($n \geq 1$) start-up of the tempering apparatus or after each $n^{th}$ application of the tempering apparatus in a tempering program. Further, the starting device, in particular a starting program, is preferably configured in a way that starting the testing method is provided automatically after a determined overall operating time of the tempering apparatus. Further, the starting device, in particular a starting program, is preferably configured in a way that starting the testing method takes place automatically after a predetermined idle time of the tempering apparatus, by letting the tempering apparatus switch on, in particular self-acting, from a stand-by mode onto execute said testing method. The starting device, in particular a starting program, is further preferably arranged in a way that starting the testing method and the type of the testing method to be performed is assigned to a certain type of tempering program. Said assignment can be permanently stored in the tempering apparatus or the testing device or can be assigned by the user, in particular by means of the input device. It can, in particular, be provided that the user automatically is informed on the testing results at the execution of the tempering programs or that a certificate is issued which provides information on the operating condition of the tempering apparatus, in particular before, during or after the execution of the tempering program. By means of said versatile starting methods, the reliability of the tempering apparatus can be improved and at the same time a testing method can be performed more flexible and comfortable for the user. Preferably, the tempering apparatus, in particular the starting device, is configured for the performance of multiple, in particular of all of said described starting alternatives.

The testing device is configured for the execution of a testing method. A testing method includes a series of processes within said testing device, which is signal-connected to said tempering apparatus, wherein by means of said processes at least one testing quantity of the tempering apparatus is determinable, which characterizes the operating condition of the tempering apparatus. Said process include, in particular, the generation of said starting signal, as well as the control of at least one temperature measurement device and the processing of the measured data. The execution of a testing method preferably takes place by means of processing at least one test program code. Further, the execution preferably takes place before or after the execution of a tempering program of said tempering apparatus. However, it is also possible and preferred that the testing method takes place in part or completely during the execution of the tempering program of the tempering apparatus. Preferably, the testing device is configured for the execution of a testing method at least in part during the execution of a tempering program. By this way, on the one hand time can be saved and, on the other hand, a test can be obtained, which individually guards the progress of a tempering program, for example by determining for each adjusted temperature value or for each approaching of a temperature value a testing quantity, which characterizes the operating condition of the tempering apparatus during said step. This allows, for example, to issue for each tempering program a detailed certificate, which improves the reliability of, for example, the performance of a PCR.

Further, the tempering apparatus preferably comprises at least one power control device, which is configured for the control and/or measurement of the power, which is put out to at least one tempering device, in particular the electrical power. Further, the testing device preferably comprises a signal-connection to said at least one power measurement device, such that the power, which is put out to such a tempering device, can be determined and can be available as data for the use in a testing method, in particular within a testing method according to the invention. Such a power measurement device for measuring an electrical power $P=U \cdot I$ can, for example, comprise a digital power-meter. In a digital power-meter, instantaneous values for current and voltage are digitized by means of a preferably high sampling rate and are computed in a calculation unit to determine the electrical power $P=U \cdot I$.

The tempering apparatus, in particular the control device, preferably comprises a timer, which preferably stands in signal-connection to the testing device. Preferably, the testing device comprises at least one timer.

The tempering apparatus and/or the testing device are, respectively, preferably configured for the execution of the testing method according to the invention.

Further features and advantages of the tempering apparatus according to the invention can be derived from the following description of the testing method according to the invention and its preferred embodiments.

The object underlying the invention is further solved by the method according to the invention for testing at least a first testing quantity of a tempering apparatus. The method can, in particular, be performed by tempering apparatus, which are configured as thermomixers, thermostats or thermocyclers.

The method according to the invention for testing at least one first testing quantity of a tempering apparatus, which serves for the tempering of at least one sample, in particular a PCR-sample, wherein said tempering apparatus comprises at least one tempering block, which is configured for the reception of at least one sample, at least one first tempering device, which is arranged for the tempering of said at least one tempering block, at least one first temperature measurement device and at least one second temperature measurement device, which are assigned to at least one control loop, wherein at least one temperature measurement device is assigned to each tempering device, at least one control device, which is configured for the control of the tempering of the at least one tempering block, an at least one first control loop, to which said at least one first tempering device and said at least one first temperature measurement device, which is assigned to said at least one first tempering device, are assigned to, comprises the following steps: Starting of the method; operating at least said first tempering device for the duration of at least a first period from at least a first time; detecting at least one measurement temperature by means of said at least one temperature measurement device, which is assigned to said first tempering device, at least at a second time; detecting at least one first testing quantity of the tempering apparatus and using said at least one measured temperature; comparison of said first testing quantity with a reference quantity.

It is an advantage of said testing method according to the invention that the operating condition of a tempering apparatus and its components, in particular the operating condition of a network of components, can be monitored, wherein said network comprises at least one first tempering device and further said at least one temperature measurement device, which is assigned to said at least one first tempering device. The detected first testing quantity can be assigned at least to said first tempering device and to at least said first temperature measurement device. In particular, said first testing quantity is assigned to said component network and characterizes its operating condition. By the comparison of said first testing quantity with a reference quantity, which, for example, can be stored in a memory device of the tempering apparatus, which is made available via an interface or which is calculated by the controlled device, the operating condition can be monitored. In particular in the case if more than one tempering devices are provided or if measurement data from at least two different temperature measurement devices are available, the operating condition of said tempering apparatus can be monitored by the comparison of two or more testing quantities, wherein, for example, a first testing quantity can be assigned to a first tempering device and a second testing quantity can be assigned to a second tempering device or a first testing quantity can be assigned to a first temperature measurement device or a second testing quantity can be assigned to a second temperature measurement device.

Preferably, in addition to the first testing quantity, that is either at least in part simultaneously or at least in part temporarily sequentially, a second testing quantity is detected. The latter can be assigned to a second temperature measurement device and/or to a second control loop which can be configured analogical to said first control loop. This offers the advantage that the operating condition of the tempering apparatus can be characterized also without using a reference quantity being present as stored data by comparing said first and said second testing quantity and by indicating a failure in the case of a deviation within a predetermined tolerance. Thereby, the reliability of the testing method and its functionality can be further enhanced.

In a first embodiment of the method according to the invention it additionally refers to the testing of a second testing quantity of the testing apparatus, wherein to said first control loop at least one second tempering device and at least said one temperature measurement device, which is assigned to said second tempering device, are assigned to, and wherein the method comprises the following steps: Operating said second tempering device for a duration of at least a first period from at least a first time; detecting at least one measurement temperature from said at least one second temperature measurement device, which is assigned to said second tempering device, at least at a second time; determining at least a second testing quantity of the tempering apparatus by using said at least one measurement temperature; comparison of said second testing quantity with a reference quantity. The method is therefore useful for such tempering apparatus, which, for example for the increasing of the tempering performance, provide at least two tempering devices, to which respectively at least one temperature measurement device is assigned to. By letting the method individually detect the measurement temperatures of said temperature measurement devices, two testing quantities can be determined, which individually or in comparison with each other give information on the operating condition.

Preferably, for said one first control loop two testing quantities are determined, such that their comparison gives information on the operating condition of the tempering devices and temperature measurement devices, which are used in said control loop. Further, by said configuration of the testing method and the tempering apparatus it can be recognized with a high probability whether a functional failure is present at a network of a tempering device and its assigned temperature measurement device. However, without further provisions it cannot be recognized whether in the case of a failure which is recognized for such a network, the cause lies in a malfunctioning tempering device or in a malfunctioning temperature measurement device. However, said problem can be solved by means of further constructive provisions that is with the tempering apparatus in a further configuration and the testing method in its second embodiment. In this case, the tempering devices and the temperature measurement devices of a control loop have to be configured to be selectively excludable from the system, and have, for example, to be configured disengageable by means of the testing device. In such a case it is, in particular, possible in a tempering apparatus, at which each control loop comprises at least two tempering devices and at least, respectively, one temperature measurement device, which is assigned to said tempering device, by means of such a configuration of the method according to the invention, to determine the individual component of the temperature measurement devices and tempering devices which is malfunctioning.

For that purpose, a control loop preferably provides the same number of tempering devices and temperature measurement devices, in particular at least two tempering devices and at least two temperature measurement devices, in particular a number of three or four and in particular preferred two. At the normal tempering operation of the tempering apparatus, the two tempering devices T1 and T2, which are assigned to at least one section of the at least one tempering block in the tempering apparatus, and the two temperature measurement devices S1 and S2, which are assigned to the respective tempering device for the regulation of temperature of a section, are used for the regulation of the temperature of said section. Thereby, T1 and S1 or T2 and S2 can, respectively, be arranged for their mutual assignment respectively closer to each other than respectively T1 and S2 or T2 and S1. For the regulation of the temperature, that is the tempering of said section, the tempering devices T1 and T2 as well as the temperature measurement devices S1 and S2 are used.

First, a temperature difference is determined, which is measured by operating the tempering device T1 within a constant period by means of the temperature measurement device S1 as first testing quantity. Further, a temperature difference is determined, which is determined within said period by operating the tempering device T2 by means of said temperature measurement device S2 as the second testing quantity. By comparison of respectively the first testing quantity and the second testing quantity with a reference quantity it can first be determined for which network of components T1, S1 or T2, S2 a malfunction is present. After it, a third testing quantity and subsequently preferably a fourth testing quantity are determined. The third testing quantity is the temperature difference, which is determined at S1 due to a temperature change by means of T2 within a predetermined period and the fourth testing quantity with the temperature difference, which is effected at the temperature measurement device S2 within said period due to tempering by means of T1. Hence, a temperature regulation of the tempering block (section) is initially exclusively performed via the network T2, S1 and optionally afterwards exclusively via T1, S2. The comparison of said third testing quantity with a further reference quantity gives information on whether a malfunctioning has occurred at the pair of component T1, S2 or T2, S1. By comparison with the first and the second testing quantity it can be reasoned, which component T1, T2, S1 or S2 provides a malfunction. If, for example the network S1, T2 provides a malfunction, which is determined by means of the first testing quantity, and the network S2, T2 does not provide a malfunction, which is determined by means of the second testing quantity, then a malfunction of the temperature measurement device S1 is present, if the network S1, T2 shows a malfunction, which is determined by means of said third testing quantity. Said diagnosis can be confirmed, if the first testing quantity, which can be determined optionally and which corresponds to the network T1, S2, does not show a malfunction, In a third embodiment of the method according to the invention it relates also additionally to the testing of a second testing quantity of said tempering apparatus, wherein said tempering apparatus comprises at least one second control loop, which is different from said first control loop, wherein to said second control loop at least one second tempering device and at least said second temperature measurement device, which is assigned to said at least one second tempering device, are assigned to, and wherein the method comprises the following steps: Operating said second tempering device for the duration of at least a first period from at least a first time; detecting at least one measurement temperature from said at least one second temperature measurement device, which is assigned to said second tempering device, at least at a second time; detecting at least a second testing quantity of the tempering apparatus by using said at least one measurement temperature; comparison of said second testing quantity with a reference quantity. The method is therefore of advantage for the tempering apparatus, which comprise two or more, preferably independent, control loops. Such tempering apparatus are used for generating a temperature gradient in the tempering block. By letting the method individually detect the measurement temperatures of the temperature measurement devices of said control loops, two testing quantities can be determined, which individually by comparison with each other or with a reference quantity give information on the operating condition.

In particular, if multiple temperature measurement devices are assigned to the tempering device for tempering apparatus, preferably a fourth configuration of the method according to the invention is used. Said method is used for detecting a difference of measured temperatures as testing quantity of a tempering apparatus, and comprises additionally to the steps of the method according to the invention the following steps:

Detecting at least one measurement temperature from said at least one second temperature measurement device at least at a second time; using said measurement temperature for the detection of said testing quantity by forming at least one difference of measurement temperatures of said first and second temperature measurement devices, and use of said difference as said testing quantity. The second time, at which the measurement temperature is detected by means of the first temperature element device, that is the second time of the first temperature measurement device, and the second time of the second temperature measurement device are preferably the same time. However, the measurements can also take place at different time points. Said difference is a measure for the deviation of the operating condition of the tested temperature measurement devices. This configuration of the method is in particular usable also in combination with the configurations of the method described above, which refer to the detection of said second testing quantity, that means that not only said first but also said second testing quantity can be a temperature difference, which was detected by means of two, in particular different or even the same, temperature measurement devices.

Preferably, an absolute value, for example a time, a temperature or a time difference or temperature difference is used as testing quantity. For that purpose a set temperature is adjusted, preferably by means of the control loop, and the temperature value, which is measured this way, is used for the testing method. In a fifth embodiment in the method according to the invention therefore comprises additionally the following steps: Applying a set temperature from at least said first time at the control loop, to which said at least one tempering device and said at least one temperature measurement device, which is assigned to said at least one tempering device, are assigned to; using the measurement temperature, which is measured at said second time, as said testing quantity. Preferably, thereby also the at least one measurement temperature is detected, which is measured by said at least one first temperature measurement device, which is assigned to said first tempering device, at said first time. It is further possible that—in particular parallel to said beforementioned step—the power input of said first tempering device is measured between said first and said second time by means of a power control device as testing quantity and is compared with reference data for the power input of said first tempering device. Preferably said second time is chosen such that the tempering block or tempering block section, which is tempered hereby, has adapted the set temperature within the limits of a tolerance. Preferably, the method comprises the step that said first period is chosen such that it comprises a delay time, for example 0 to 900 seconds, 10 to 50 seconds or preferably 20 to 40 seconds, which follow up to the time point, at which the tempering block or tempering block section, which is to be tempered, has reached the set temperature within a tolerance, to achieve a stable temperature measurement. For that purpose, preferably at times after said first time the measurement temperature is repeatedly detected by means of said first temperature measurement device, for example periodically. Said set temperature plus a tolerance is preferably used as said reference quantity. However, it is also possible that said reference quantity is different, in particular smaller, than said set temperature, such that a comparison of the measurement temperature with the reference quantity can take place in particular before reaching the set temperature at the tempering block, such that a shortened test method is possible, which can lead in particular to a shortened overall duration of the testing method.

Alternatively to an absolute value, for example a time, temperature or difference, also a temporal change of the values, for example a temperature change velocity or a rate, can be used as testing quantity. In this way, the performance parameters, which are relevant for the operation of a tempering apparatus, can be determined and the capability of the apparatus can be determined. Said temporal change of values can be described by the quotient of the value difference divided by the time difference. Said quotient can be, for example, the temperature difference divided by the time. For the determination of said quotient, a period can be predefined and the temperature difference can be measured, which is reached at the expiry of the predefined period. The variable quantity in this case is the temperature difference. Alternatively, the temperature can repeatedly be measured and the time point and therefore the period can be detected, at which a predefined temperature or temperature difference is reached. The variable quantity in this case is the time or the period. As the testing quantity in both cases either the quotient or the variable quantity can be used. If the variable quantity is chosen as the testing quantity, then the respectively predefined (constant) value, for example a fixed temperature difference, will also be used for the reference quantity, which is used for the comparison with the testing quantity. The use of the variable quantity as the testing quantity offers in particular the advantage that the step of calculation of forming of a quotient and also computation time is saved.

For said purpose, the method according to the invention in a sixth embodiment preferably comprises the steps: Detecting at least one measurement temperature from said at least one temperature measurement device, which is assigned to said tempering device, at a third time; forming the difference between two measurement temperatures, from which the first was measured at said second time and the other was measured at said third time; forming of a second period, which corresponds to the difference of said third time and said second time; and using said difference between two measurement temperatures or said second period as said first testing quantity. Said third time for all embodiments of the method preferably lies after said second time.

Alternatively to the sixth embodiment in the method according to the invention the seventh embodiment preferably comprises the steps: Detecting of at least one measurement temperature from said at least one temperature measurement device, which is assigned to said tempering device, at a third time; forming the quotient of the difference of two measurement temperatures, from which the one was measured at said second time ant the other was measured at said third time, at a second period, which corresponds to the difference of said third time and said second time, and using said quotient of the difference and the second period as said first testing quantity.

As described above, a period can be predefined and the temperature difference can be measured which arises upon expiration of the predefined period. For that purpose the method in an eighth embodiment preferably comprises the steps: Using a predefined second period; using the sum of said second time and said predefined second period as said third time. In this case, the second period is kept constant and the temperature difference at said first temperature measurement device at the begin and the end of said second period is detected. Said third time is at the determination of a quotient preferably chosen such that the tempering block does not yet reach the set temperature. Then, the temperature difference or the quotient during a period is detected in which the temperature of the tempering block changes continuously. However, the third time can also be chosen such that the tempering block within a tolerance has already reached the set temperature.

As described above, it is also possible and preferably provided that a time difference or a quotient is used as said first testing quantity wherein the difference of the measurement temperatures is kept constant, as it is determined, at which third time said temperature difference will be measured. For this purpose the method in a ninth embodiment preferably comprises the steps: Repeated detecting of at least one changing measurement temperature from said at least one temperature measurement in the device, which is assigned to said tempering device, at times after said second time; comparison of said changing measurement temperature with a comparison temperature; detecting a time, at which said changing measurement temperature has reached said comparison temperature within a tolerance and using said time as said third time. The comparison temperature is preferably said set temperature or another, predefined temperature, for example a temperature which is stored in the tempering apparatus.

Depending on if a variably quantity or respectively said quotient according to the sixth or, respectively, the seventh embodiment of the method is detected, as said temperature difference or said second period is kept constant, other types of function failures of the tempering apparatus can be detected. By this way, the flexibility of the testing method is enhanced.

The tempering, in particular at the sixth or seventh embodiment of the method, can either take place by establishing a set temperature at the control loop or by establishing a constant power to the tempering device. At a constant temperature difference, the method according to the tenth embodiment therefore preferably comprises the step: Applying a set temperature from at least said first time and for at least the duration of said first period to said first control loop, to which are assigned said at least one first tempering device and said at least one first temperature measurement device, which is assigned to said at least one first tempering device. Thereby, said comparison temperature preferably is said set temperature. Further, in the case of a constant temperature difference it is preferably provided that the method in an eleventh embodiment comprises the step: Operating said at least one first tempering device for the duration of at least said first period from at least one first time with constant power.

For further enhancing of the reliability of the testing method and its functionality it is preferably provided that one second testing quantity is detected, which is compared either with said first testing quantity or with a reference quantity.

For the case, that at least two different testing quantities are detected by the testing method, it is preferred that the method comprises at least one of the both steps: Using said second testing quantity as reference quantity for comparison with said first testing quantity; using said first quantity as reference quantity for comparison with said second testing quantity.

For all embodiments or modifications of the method it is preferred that said reference quantity is a comparison temperature, which for example is stored in a storage device of the tempering apparatus, or which is supplied to the tempering apparatus via a data interface.

The starting of the method preferably takes place manually by the user, preferably via an input panel at the tempering apparatus. Preferably, the starting of the method takes place selectively either manually by the user or automatically. Further, the starting of the method takes place preferably automatically for each measurement, which is carried out by means of said tempering apparatus at said at least one sample, in particular to one, in particular each, execution of a tempering program for at least one sample, in particular before, after or during an execution of a tempering program. Preferably, the starting of the method takes place automatically in regular periods automatically after each $n^{th}$ ($n\geq1$) starting up of the tempering apparatus or at each $n^{th}$ application of the tempering apparatus. Further, it is preferred that the starting of the method is provided automatically after a predetermined overall operation time of the tempering apparatus. Further, it is preferred that the starting of the method takes place automatically after a predetermined idle time of the tempering apparatus, as the tempering apparatus switches on itself automatically from a standby mode too perform said testing method. In this way the reliability of the tempering apparatus can be enhanced and at the same time a testing method can be run in a comfortable way for the user. Preferably the tempering device is configured for the realization of several, in particular all, of said described starting alternatives.

The method according to the invention is preferably configured for the purpose to provide a short total time for its application, which is preferably shorter than 40 minutes, preferably shorter than 30 minutes, preferably shorter than 25 minutes, especially preferred shorter than 20 minutes, even more preferred shorter than 15 minutes, even more preferred shorter than 10 minutes, even more preferred shorter than 9.5 minutes and even more preferred shorter than 6 minutes. Most preferred the total time of the method according to the present invention is under 5 minutes. Further, the tempering apparatus according to the invention, in particular also its testing device, is preferably configured for the execution of such a testing method with such a short total time. A short total time offers the advantage that more time is available for the execution of the primary function of a tempering apparatus, namely the execution of at least one tempering program. In this way, the work flow at the application of a tempering apparatus, which runs the testing method according to the invention, is less delayed and the use of said tempering apparatus becomes more efficient and comfortable. Further, a short total time allows for carrying out the testing method more often, in particular automatically. Thereby, the reliability of the tempering apparatus is further improved. For the case, that the testing method is completely run during the application of a tempering program, the duration of the method can be described as zero.

The tempering apparatus according to the invention and/or the method according to the invention further preferably provides a documentary function, by means of which data can be permanent recorded, that is for example permanently respectively to a power failure. Preferably, the tempering apparatus provides a documentary device, which can comprise a storage device or parts of a storage device, which is also used for the storage of other date. Said documentary device is preferably arranged in said tempering apparatus, but can also be configured as external device, for example as part of an external PC, which is connected to the tempering apparatus via a data interface. The documentary device preferably serves for the storage of a testing log file, which provides data base entries, which for example comprise the date, the time of day, serial number, user and/or the testing result (for example if passed/ failed). Correspondingly, the method preferably comprises the step: Entering of at least one data base entry in a documentary device of the tempering apparatus. By the documentation of testing results the maintenance and thereby the reliability of the apparatus can be improved.

The result of a testing device is preferably put out to the user. This can take place visually, for example via an input panel of the tempering apparatus, and/or acoustically, for example via a loudspeaker of the tempering apparatus. Further it is preferred that the tempering apparatus according to the invention and/or the method according to the invention comprises a certification function, by means of which a certificate of a performed testing method can be generated. For said purpose, the tempering apparatus is preferably configured for the output of a certification data set in a certificate, by putting out all representing certification data for example visually via an optical input panel of the tempering apparatus or via a data interface to an external device, for example to a PC, a mobile data storage or to a printer. Correspondingly, the method preferably comprises the step: Generation of a certificate of certification data. Said certification data can contain a text, which is definable by the user or a predetermined text, as well as a header with the date, the time of day, the user name, serial number of the apparatus or the type of apparatus. Further, said certification data preferably comprises at least one testing result of a testing method performed before, for example an overall result and one or more parts of results.

It is further possible that the method is executed multiple times and sequentially and in particular by means of different components at least in part simultaneously and repeatedly, and it is further preferred that multiple different of the described embodiments of the method are combined. At a combined method, the method according to the invention is executed multiple times, namely in at least one of the described embodiments. At a combined method, preferably at least one method according to an embodiment for the determination of an absolute value as testing quantity is used together with at least one method according to an embodiment for the determination of a value change (said sixth or seventh embodiment of the method) as testing quantity, to determine one or more testing quantities. Thereby, a more reliable overall testing of the operating condition of the tempering apparatus can be achieved.

Further features and advantages of the testing methods according to the invention can be derived from the above description of the tempering apparatus according to the invention and its embodiments.

The method according to the invention is preferably provided for the execution with at least one tempering apparatus according to the invention. However, it is also possible and preferred that said method according to the invention is executed with another tempering apparatus.

Further features and advantages of the invention can be derived from the subsequent description of the figures and the figures. Same reference signs in the figures substantially characterize the same components or method steps, to avoid repetitions.

FIGS. 1 to 7 are schematic drawings of different embodiments of the tempering apparatus according to the invention.

FIGS. 7 to 12 schematically show the procedure of method according to the invention in different embodiments.

Figure 13:
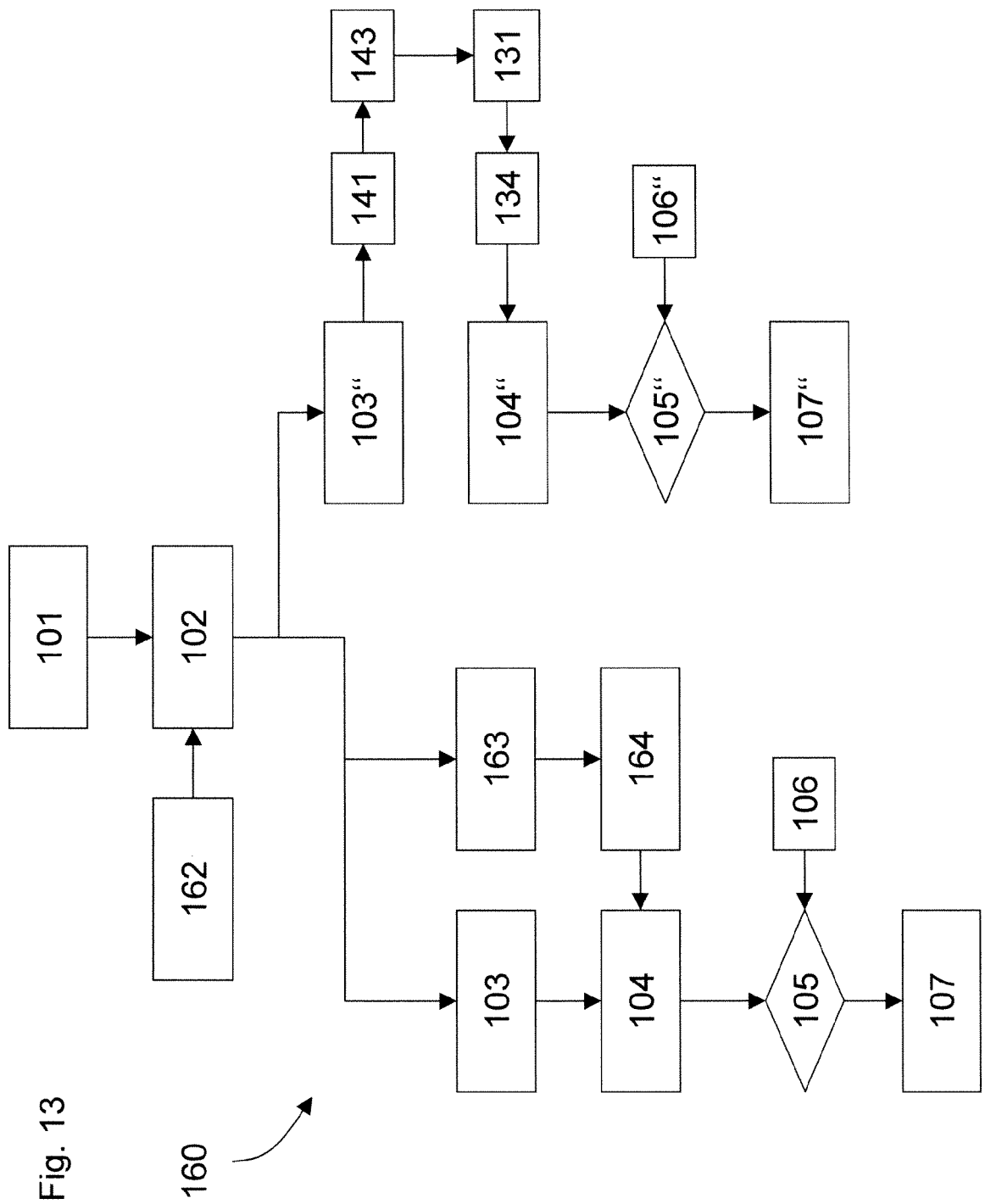

FIG. 13 schematically shows the procedure of a method, which combines the method according to the invention in two embodiments into a combined method.

The tempering apparatus 1 is a thermocycler, which is configured for the automatic performance of a polymerase chain reaction (PCR) in a plurality of PCR-samples. The theromocycler 1 comprises a housing 2 and a heatable cover 3. It comprises a substantially cube-like tempering block 4, which is a component made integrally from metal. The tempering block 4 provides at its upper side a plurality of receptacles 5, which are configured for the reception of a plurality of sample vessels, for example of a PCR-plate. The sample vessels and the receptacles 5 are configured such that a preferably large contact area is reached between the exterior wall of the sample vessels and the interior wall of the receptacles 5, a contact area which is the same for each sample vessel, to guarantee an optimal and reproducible heat transfer between the tempering block 4 and the sample vessel. The tempering 4 is heatable via the tempering device 6, which is a Peltier element. At the tempering block 4 further to temperature measurement devices 7, 7' are mounted, by means of which the temperature of the tempering block can be measured.

The control of the tempering apparatus 1 takes place by means of the control device 8. The latter in particular carries out the control of the tempering of the tempering block 4.

The Peltier element 6 is in a large area contact with the underside of the tempering block 4 such that upside of the Peltier element 6 a plurality of receptacles 5 are located.

As a functional component of the tempering control the control device 8 comprises a control loop 9, to which said tempering device 6 and said two temperature measurement devices 7 are assigned to. The control loop 9 comprises the circuits of the controller 10, which receives as control a variable of the control loop 9 two of the actual temperature values, which are measured by the temperature measurement devices 7, 7' via the connections 11, 13. The testing quantity is formed for example by the formation of an average value of the both actual temperature values. By comparison, in particular by formation of a difference of the actual temperature values with the adjusted temperature set values (target temperature), the controller 10 determines a control value, which finally determines at which power the tempering device 6 is operated via the connection 12.

The tempering apparatus comprises a testing device 14, by which means a testing method can be executed, by means of which at least one testing quantity is detectable, which characterizes the operating condition of the tempering apparatus. The testing device 14 is arranged within the tempering apparatus 1 and is structurally integrated in the control device 8. Via the signal line 15, the controller 10 and the signal line 11 the testing device 14 is signal-connected with the temperature sensor 7 and analogically with the second temperature sensor 7'. Thus, the testing device comprises a signal-connection to the control loop 9, in particular to the controller 10, and is in particular configured to control the power, which is put out to the tempering device 6, by influencing the control value of the control loop. An advantage of the use of two temperature measurement devices 7 and 7', which are assigned to a tempering device 6, is that an additional data source can be generated, which can give information about the operating condition of the apparatus in a way that not only the total break-down of a component can be detected but also performance deviations of the components can be detected. The sensor 7' not only measures the temperature which is controlled by means of the tempering device 6, but also at the other hand delivers a comparison value for the data, which are measured by means of the sensor 7. By means of the described signal-connections of the testing device 14 with the components of the tempering apparatus, a testing method can be run with the tempering apparatus, without requiring costly additional hardware. In this way, the reliability of the testing device and the tempering apparatus is improved.

A section of a storage device (data storage, not shown) is assigned to the testing device by having stored a program code for the execution of a testing method, in particular the testing method according to the invention. Further, another section of a storage device is assigned to the testing device 14, which stores the results of at least one testing method. The testing device 14 further comprises a starting device 18 for the automatic starting of a testing method, wherein said starting device is in signal-connection with said testing device, such that an automatic starting of said testing method is possible.

The starting device preferably comprises a circuit logic, which is configured in the embodiment for executing the testing method after each application of a tempering program, which for example can exist for performing a PCR. Also the starting device is structurally integrated in the control device 8.

Figure 2:
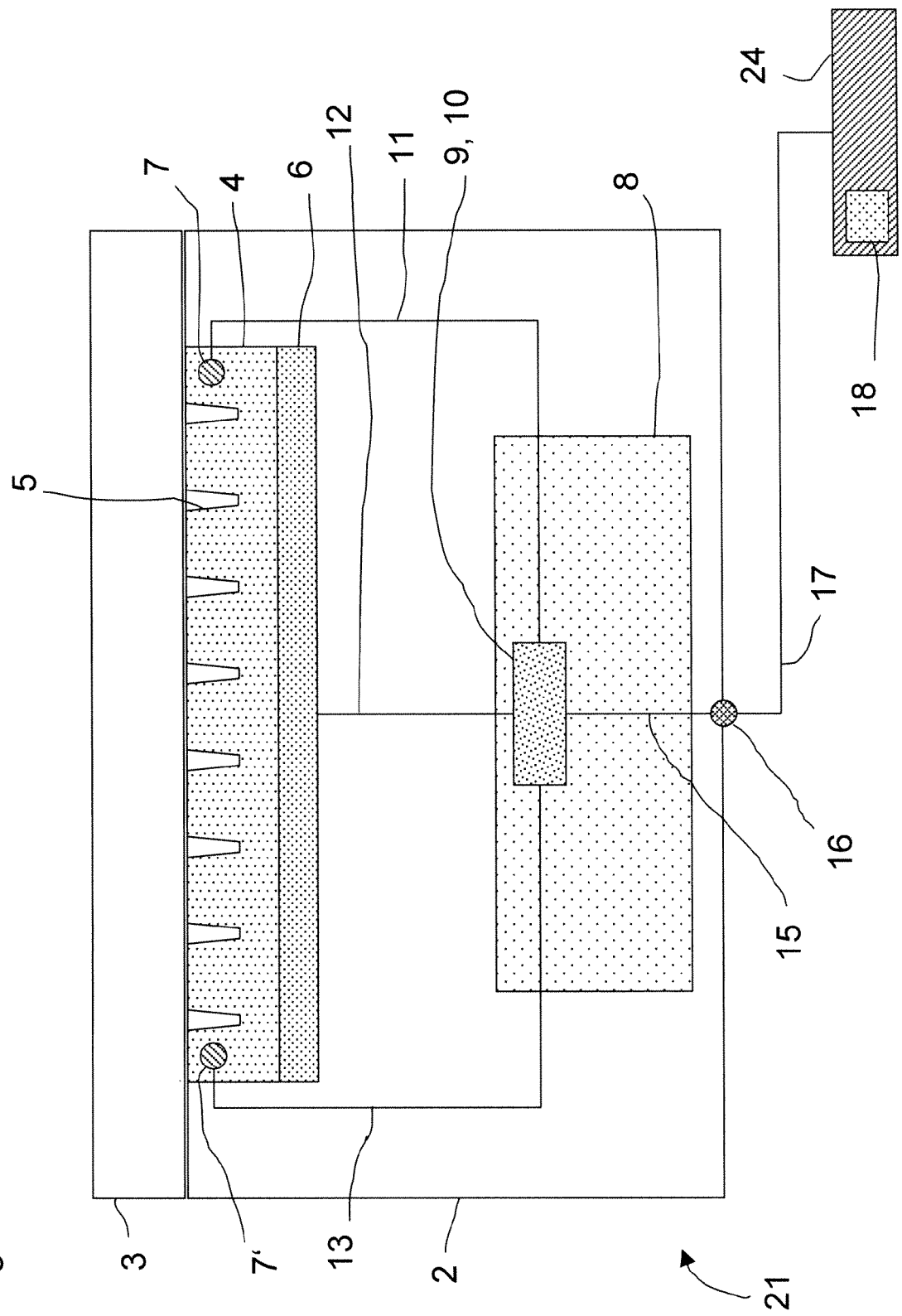

In FIG. 2, the embodiment of the tempering apparatus according to the invention, the thermocycler 21, comprises a testing device 24, which is realized as an external testing device. The testing device 24 is signal-connected to the control device 28 via a signal line 17 and a signal interface 16, and signal-connected to the temperature measurement device 7 via the signal line 15, the controller 10 and the signal line 11, and in a similar way signal-connected to the sensor 7' and the tempering device 6. Also in this embodiment for performing a testing method the present structure of the tempering apparatus, in particular the sensors, are used such that no costly additional hardware is required.

The testing device 24 can be integrated in an external control device, for example into an PC, by means of which a central control of the testing methods of different tempering apparatus can take place. Preferably the testing device 24 is integrated into a laboratory-information-management-system (LIMS). The external embodiment in particular offers the advantage that testing methods, in particular methods according to the present invention, can easily be adapted or changed and that the testing results are more directly available for an external data evaluation and surveillance.

Figure 3:
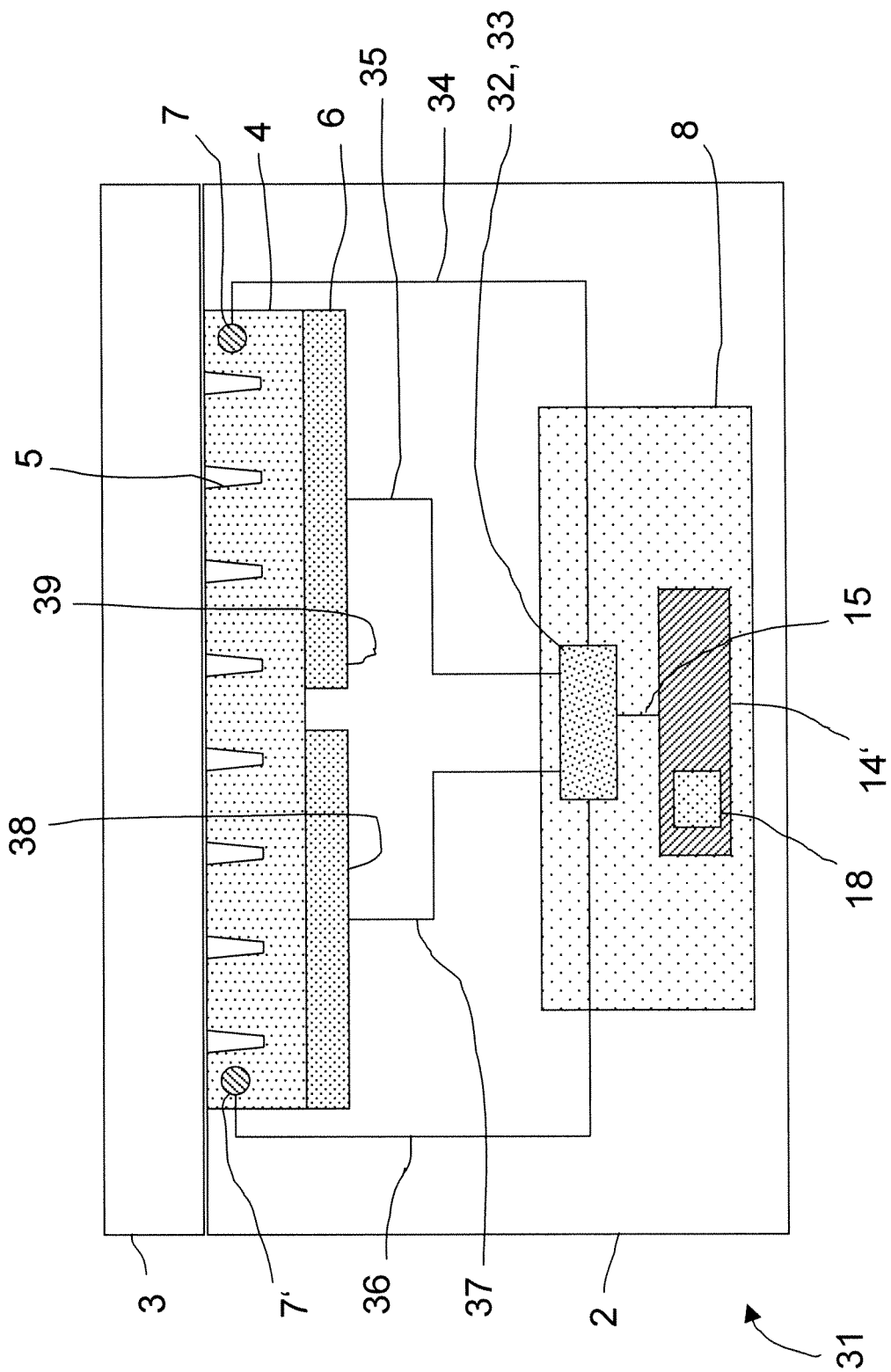

FIG. 3 shows a tempering apparatus (thermocycler) 31, which comprises a control loop 32, to which a first Peltier element 38 and a second Peltier element 39 are assigned. Further, the temperature measurement devices 7 and 7' (temperature sensors) are assigned to the control loop 32, whereby the temperature sensor 7 is assigned to the tempering device 39 and the temperature sensor 7' is assigned to the temperature device 38. The temperature of the tempering block 4, which is measured by the temperature sensor 7 thereby is such influenced substantially by the tempering device 39, which is arranged closer to said sensor 7 than the tempering device 38. Accordingly, the temperature, which is measure by the sensor 7' is more strongly influenced by the more closely arranged tempering device 38. By that assignment of the temperature sensor 7 to the Peltier element 39 and the sensor 7' to the Peltier element 38, numerous testing methods can be performed, which improve the reliability of the tempering apparatus 31. On the other hand, the possibilities exist to generate by means of said two tempering devices 38, 39 a temperature gradient along the receptacles 5.

The testing device 14' is signal-connected to the temperature sensor 7 via the signal line 15, the controller 33 and the signal line 34 and signal-connected to the tempering devices 39 via the signal line 15, the controller 33 and the signal line 35. Correspondingly, the testing device 14' is signal-connected to the sensor 7' and the tempering device 38. The testing device 14' can be configured for temporarily switching off the tempering device 38 or the tempering device 39, such that control takes place with only one tempering device. In this way, possibilities for further testing methods arise, which improve the reliability of the tempering apparatus by giving more detailed information about the operational status.

Figure 4:
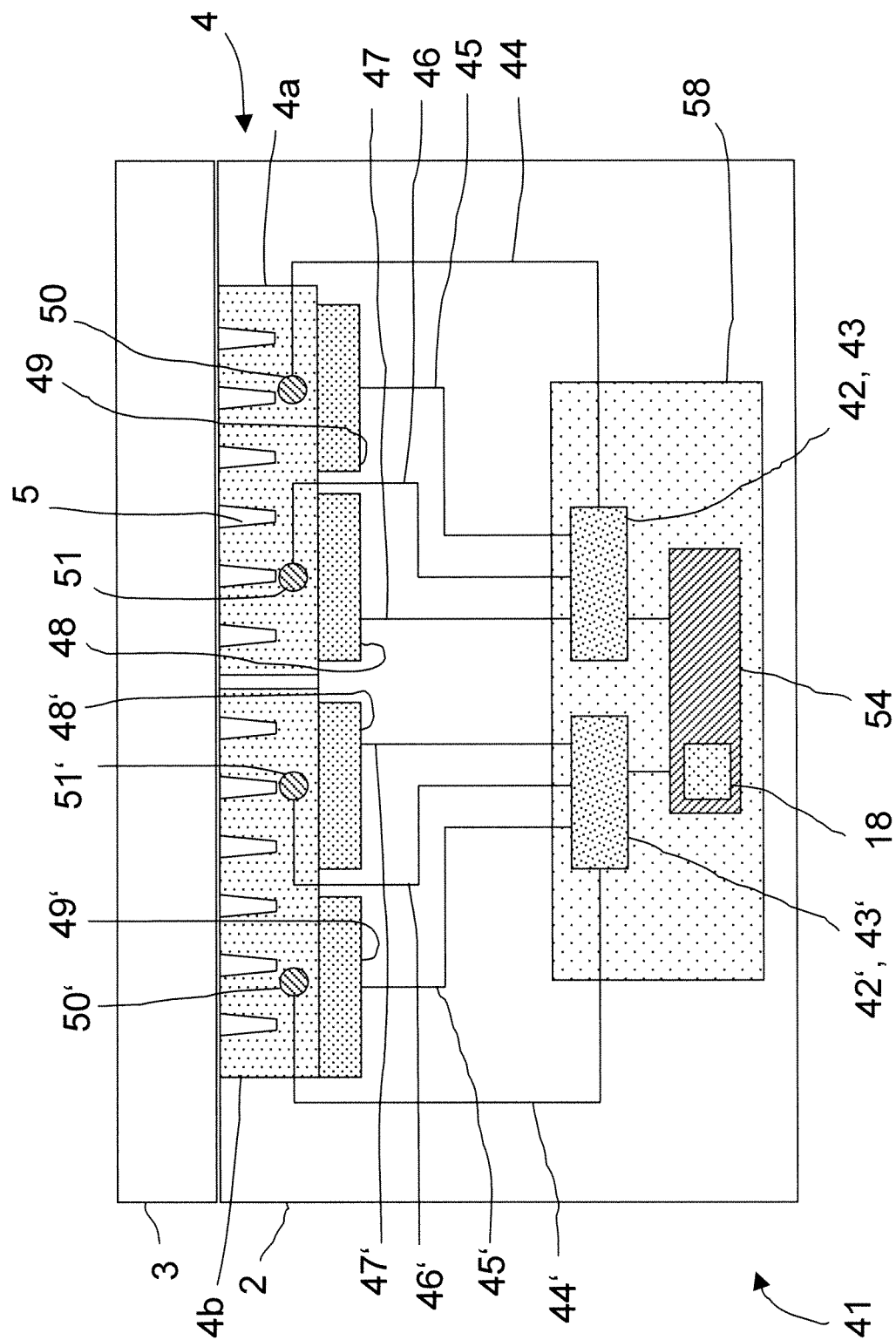

FIG. 4 shows a tempering apparatus 41, which comprises the two control loops 42 and 42', wherein to each control loop two tempering devices and two temperature measurement devices are assigned to, and wherein to each tempering device one temperature measurement device is assigned to. Thereby, the tempering block 4 is divided into two sections 4a and 4b, which are separated by a material of worse heat conductibility, for example air. Thereby, interfering influences between the control loops 42 and 42' are reduced, in particular interfering control oscillations. The control loop 42 comprises the Peltier elements 48 and 49 as actuating members, which put a temperature on the section 4a of the tempering block, which are measured by the temperature sensor 51, which is assigned to the tempering device 48, and the temperature measurement device 50, which is assigned to the tempering device 49. Said actual temperature values are transferred to the controller 43 of the control loop 42, whereby the control loop is closed. The control loop 42' is configured analogically. The testing device 54 comprises signal-connections to the control loops 42 and 42' as well as signal-connections to the temperature sensors 50, 51, 50', 51'. By said arrangement of components in the tempering apparatus 41 it is possible to provide further methods, in particular methods according to the present invention, for testing the operating condition in the tempering apparatus, whereby the reliability of the tempering apparatus 41 is improved.

Figure 5:
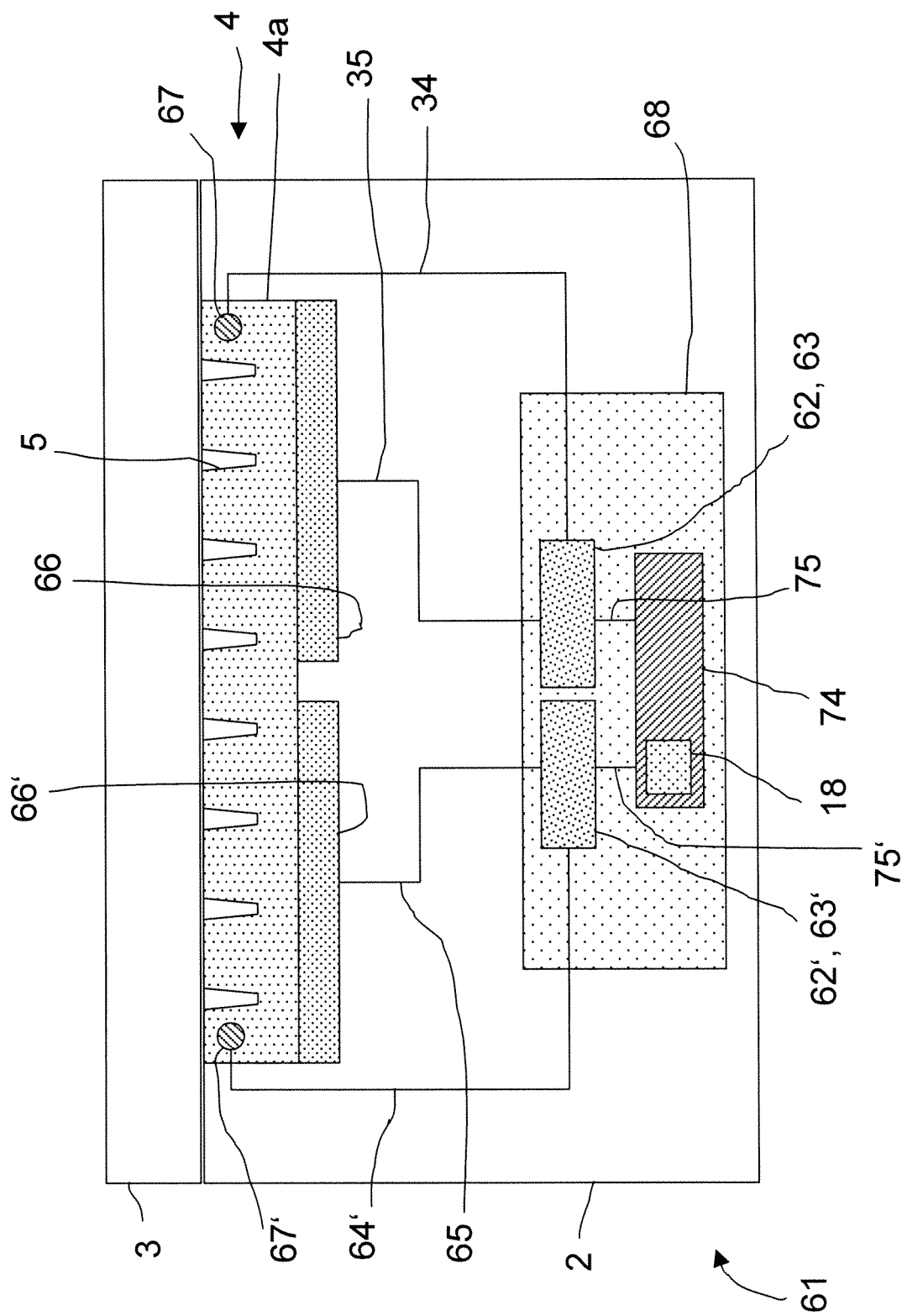

FIG. 5 shows the tempering apparatus 61, which comprises two control loops 62 and 62', wherein to each control loop one tempering device and one temperature measurement device is assigned to.

Further, to each tempering device exactly one temperature measurement device is assigned to. To the control loop 62 the Peltier element 66 is assigned to, which tempers the section 4a of the tempering block 4, to generate a temperature in the tempering block, which is measured by the temperature sensor 67, which is assigned to the tempering device 66 of the control loop 62, and which is transferred as the temperature actual value to the controller 63 of the control loop 62, whereby the control loop is closed. The control loop 62' is configured analogically. Instead of a tempering block divided into sections, also an integral tempering block 4 can be used. The testing device 74 is signal-connected to the temperature sensor 67 by means of the signal line 75, the controller 63 and the signal line 64. Analogically the testing device 74 is signal-connected to the temperature sensor 67'. Further, the testing device 74 comprises respectively one signal-connection to the control loops 62 and 62' and to the tempering devices 66 and 66'. In this way, different testing methods can be performed, as described, by means of the components which are signal-connected to the testing device 74, for the thermocycler 61, whereby its operational status can be reliably monitored.

Figure 6:
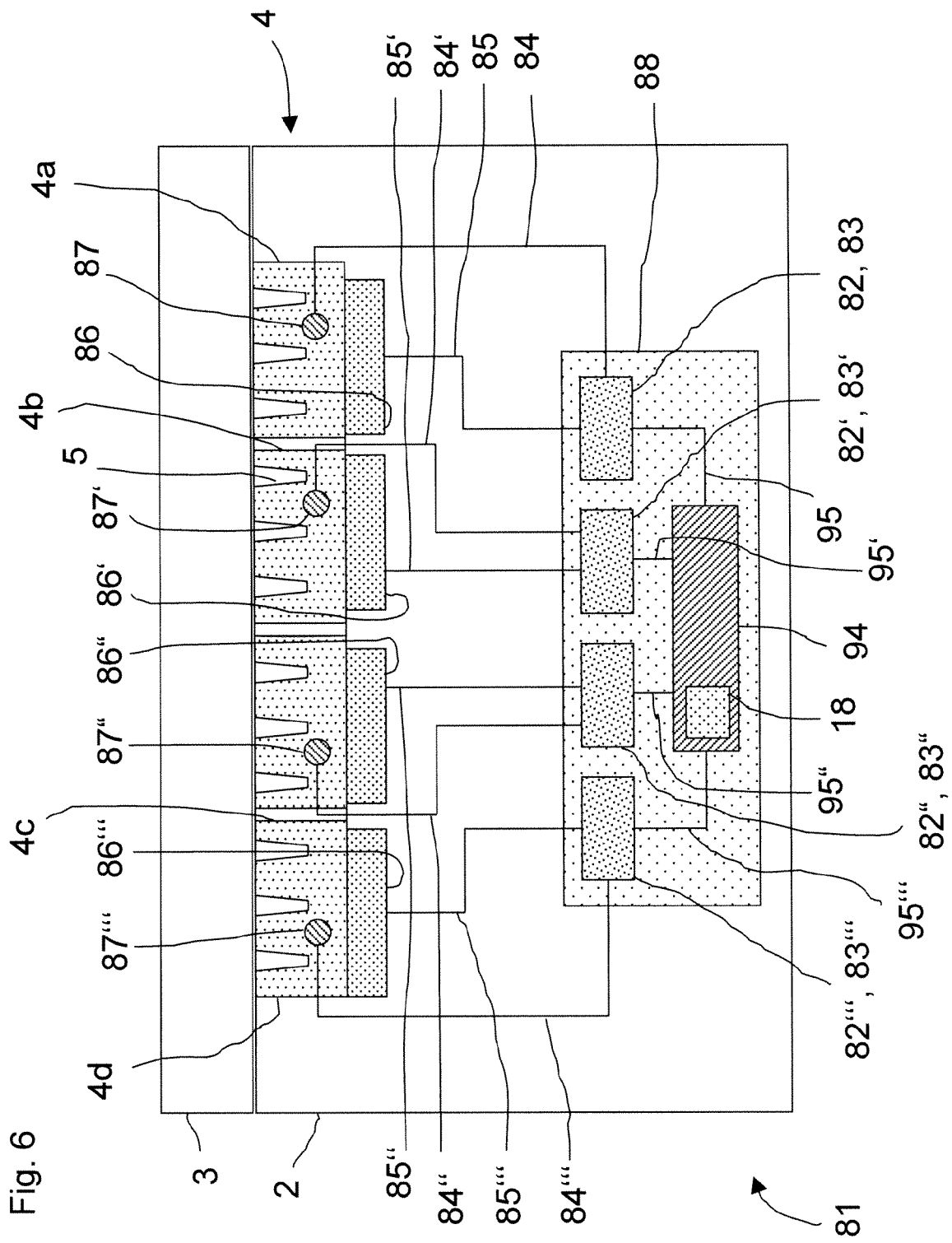

FIG. 6 shows the thermocycler 81, whose tempering block 4 consists of four sections 4a, 4b, 4c and 4d, wherein each tempering block section is tempered by one tempering device, and is assigned to one own control loop. To the control loop 81 is assigned the Peltier element 86, which generates in the section 4a of the tempering block 4 a temperature which is measured by the temperature sensor 87 and is transferred as temperature actual value to the controller 83 of the control loop 82, whereby the control loop is closed. The control loops 82', 82" and 82''' are configured analogically. The testing device 94 is signal-connected to the temperature measurement device 87 via the signal line 95, the controller 83 and the signal line 84 and signal-connected to the tempering device 86 via the signal line 95, the controller 83 and the signal line 85. analogically, the testing device is signal-connected to the corresponding components of the control loops 82', 82" and 82'''. By means of said signal-connections, numerous test methods, in particular test methods according to the invention, can be executed with the tempering apparatus 81, which monitor its operational status, and which therefore improve its reliability.

Figure 7:
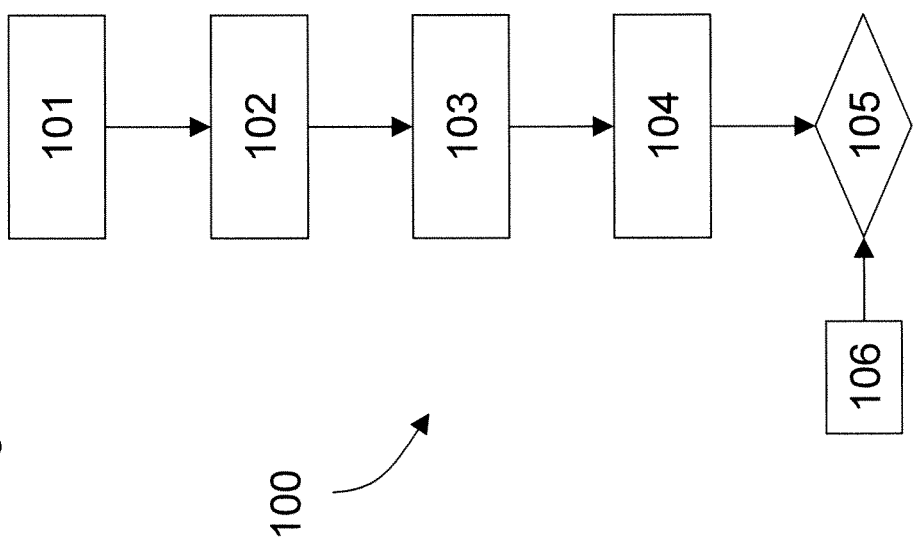

FIG. 7 shows schematically the procedure of the method 100 for the testing of at least one first testing quantity of a tempering apparatus. Said tempering apparatus, which is appropriate for the execution of the method and which is in particular the testing device according to the invention and which can correspond to one of the configurations according to FIGS. 1 to 6 is configured for the tempering of at least one sample, in particular a PCR-sample. For that purpose, the tempering apparatus comprises at least one tempering block, which is configured for the reception of at least one sample, comprises at least one first tempering device, which is arranged for the tempering of said at least one tempering block, at least one first temperature measurement device and at least one second temperature measurement device, wherein to each tempering device at least one temperature measurement device is assigned to, at least one control device, which is configured for the control of the tempering of the at least one tempering block, preferably a timer, and at least one first control loop, to which said at least one first tempering device and said at least one first temperature measurement device, which is assigned to said at least one first tempering device, are assigned to.

The method 100 comprises the steps: 101 starting of the method; 102 operation of at least said first tempering device for the duration of at least one first method from at least one first time; 103 detecting at least one measurement temperature from said at least one first temperature measurement device, which is assigned to said first tempering device, at least to a second time; 104 determining at least one first testing quantity of the tempering apparatus by using said first one measurement temperature; 105 comparison of said first testing quantity with a reference quantity. At the method 100, a quantity which is stored in the tempering apparatus and predetermined is used as the reference quantity according to step 106.

Figure 8:
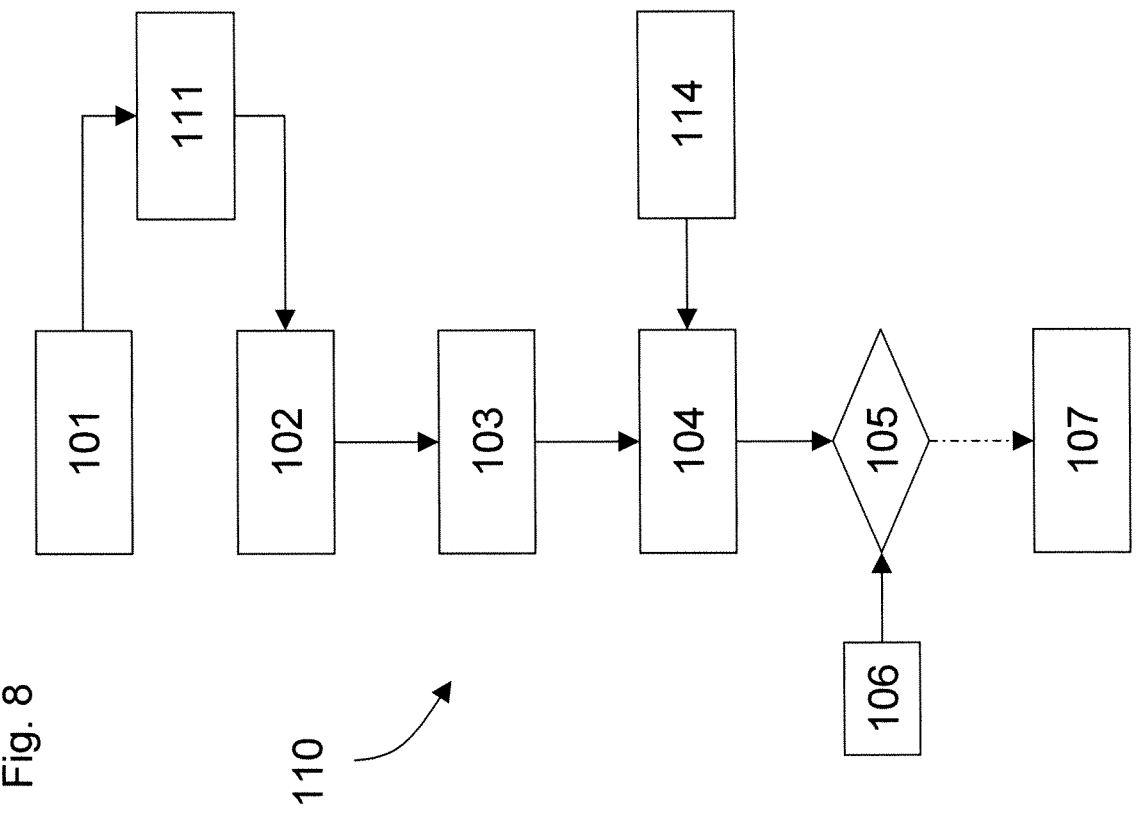

The method 110 shown in FIG. 8 shows a configuration of the method 100 which additionally to the steps 101 to 105 comprises the steps: 111 applying a first set temperature from at least said first time to said control loop, to which said at least one tempering device and said at least one temperature measurement device, which is assigned to said at least one tempering device, are assigned to; 114 use of the measurement temperature, which is measured at said second time, as said testing quantity. Step 111 causes the control loop to temper the tempering block, that is to heat or to cool, to reach a set temperature of the tempering block. The second time of the measurement of the temperature, which is then used as testing quantity (step 114) can be chosen such that the change of the temperature of the tempering block is monitored for example by means of said temperature measurement device. For that purpose, it is measured as long as within a predefined limit value no further changes occur any more, whereby the temperature is considered to be adjusted at least after a further awaiting of a delay time and the temperature measurement of the step 103 takes place. As alternative for monitoring the temperature value also a latency time (delay time) can be used, during which a stable temperature establishment is normally expected, in particular under consideration of the starting temperature and the set temperature and in particular under consideration of the history of the temperatures at the tempering block. Said latency time can for example be 30 seconds. If in step 105 a deviation of the testing quantity, which was determined in step 104, here a temperature from the predefined and to be expected referenced quantity (step 106) is determined that the testing result is considered negatively and is correspondingly put out to the user.

Correspondingly, the method 110 comprises the step 107 which provides that the testing result is put out by the testing device. This preferably takes place visually, for example via a display at the tempering apparatus or via an external output device which can be, for example, the display of an external PC, which can be signal-connected to the testing device via a data interface. The testing method 110 can be performed in particular by a testing device of the tempering apparatus according to the invention. Further, the testing results are electronically stored and documented, for example by means of a documentation device of the tempering apparatus according to the invention or on an external PC. The assignment of at least one temperature measurement device to said tempering device to a network allows to monitor the operational status of said network. The comparison according to step 105 of the measured testing quantity for example of the temperature which pends at the sensor at a certain time, with a predetermined comparison quantity, which is expected to occur under normal operating condition of the tempering apparatus, gives information about if an operational malfunction at said network is present or not. This way, the break-down of said component network can be detected. In particular, if the starting of the method takes place automatically, for example after each tenth execution of a tempering program, the reliability of the tempering apparatus can be improved.

Figure 9:
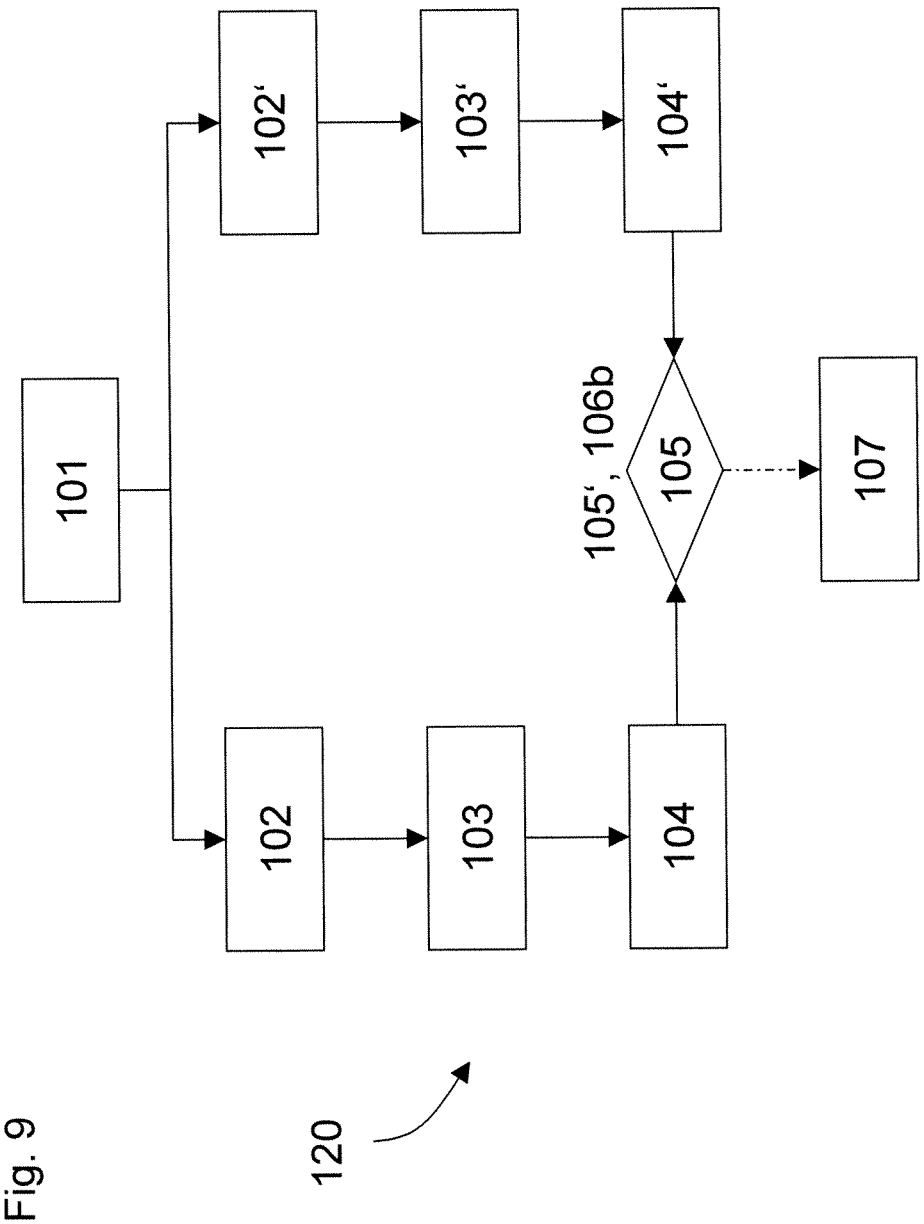

FIG. 9 shows the method 120, which additionally to testing of a first testing quantity according to the steps 101 to 105 refers to the testing of a second testing quantity of said tempering apparatus. The method is for example appropriate for a tempering apparatus, to whose first control loop at least one second tempering device and at least one second temperature measurement device, which is assigned to said at least one second tempering device, are assigned to. Further the method is appropriate for a tempering apparatus, which comprises at least one second control loop, which is different from said first control loop, wherein to said second control loop at least one second tempering device and at least one second temperature measurement device, which is assigned to said at least one second tempering device, are assigned to. Examples for such tempering apparatus are the thermocyclers shown in the FIGS. 3 to 6.

The method 120 comprises the steps: 101 starting of the method; 102 operation of at least said first tempering device for the duration of at least one first period from at least one first time; 103 detecting at least one measurement temperature from said at least one first temperature measurement device, which is assigned to said first tempering device, at least at a second time; 104 detecting at least one first testing quantity of the tempering apparatus by using said at least one measurement temperature; 105 comparison of said first testing quantity with a reference quantity, which is said second testing quantity (step 106b). Further, the method 120 provides that simultaneously or not simultaneously additionally to the steps 102 to 105 the steps are performed: 102' operation of said second tempering device for the duration of at least a first period from at least a first time; 103' detecting at least one measurement temperature from said at least one second temperature measurement device, which is assigned to said second tempering device, at least at a second time; 104' determining at least one second testing quantity of the tempering apparatus by using said at least one measurement temperature; 105' comparison of said second testing quantity with a reference quantity, which is said first testing quantity (step 106b). Alternatively or additionally, each testing quantity can be compared with a stored reference quantity. An advantage at the determination of the second testing quantity and therefore an advantage of the method 120 is that the tempering and temperature measurement devices can monitor each other, such that a better monitoring of the operational status of the tempering apparatus is possible, which therefore becomes more reliable.

Figure 10:
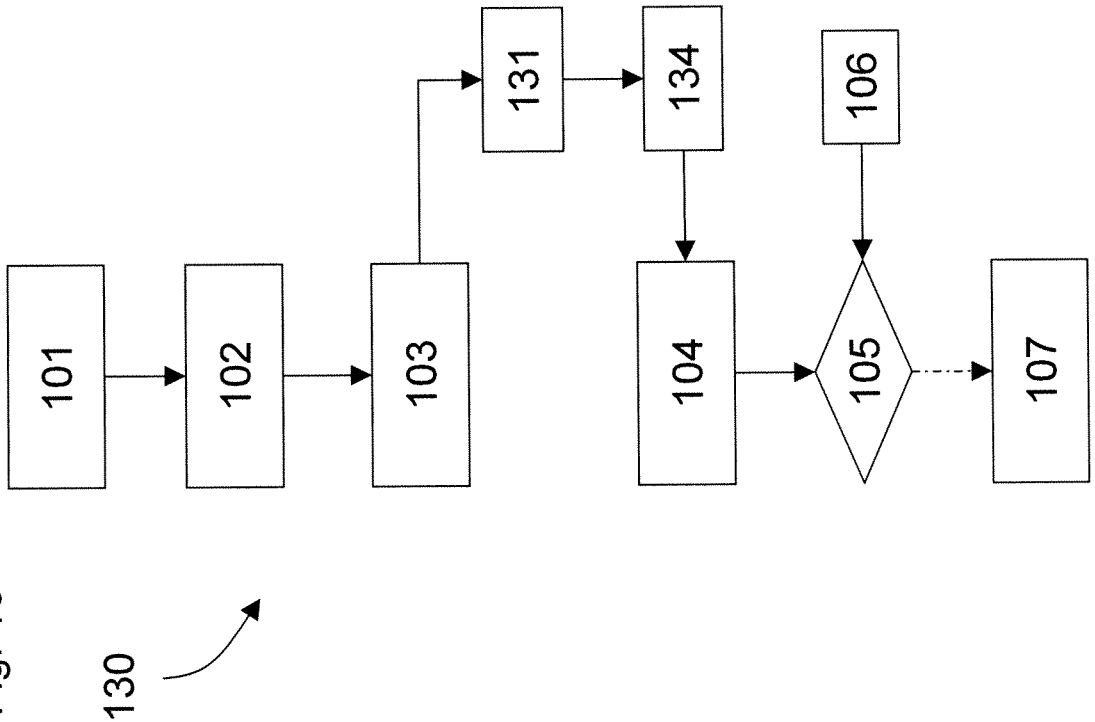

FIG. 10 shows the method 130, which additionally to the method steps 101 to 105 comprises the steps: 131 detecting at least one measurement temperature from said at least one temperature measurement device, which is assigned to said tempering device, at a third time; 134 forming the difference of two measurement temperatures, from which the one was measured at said second time and the other was measured at said third time, forming of a second period, which corresponds to the difference of said third time and said second time, and using said second period as said first testing quantity. The testing quantity "period" is determined in relation to a predefined (constant) temperature difference as change of values. Also the reference quantity, which is used for the comparison with said testing quantity, was determined and defined in relation to said constant temperature difference. Therefore a quotient exists, even if it is not explicitly calculated in said embodiment of the method. This has a dimension of a temporal change of values, in particular of a rate and in particular of a temperature change velocity. By means of such a (temporal) change of values not only the break-down of a network of tempering device and at least one assigned temperature measurement device can be determined but also according to method 140 the capability of said network can be tested. A temperature difference, time difference or the quotient of both values is determined by having either a time difference predefined and determining the resulting temperature difference, or alternatively by determining, in which time a predetermined temperature difference is formed.

Figure 11:
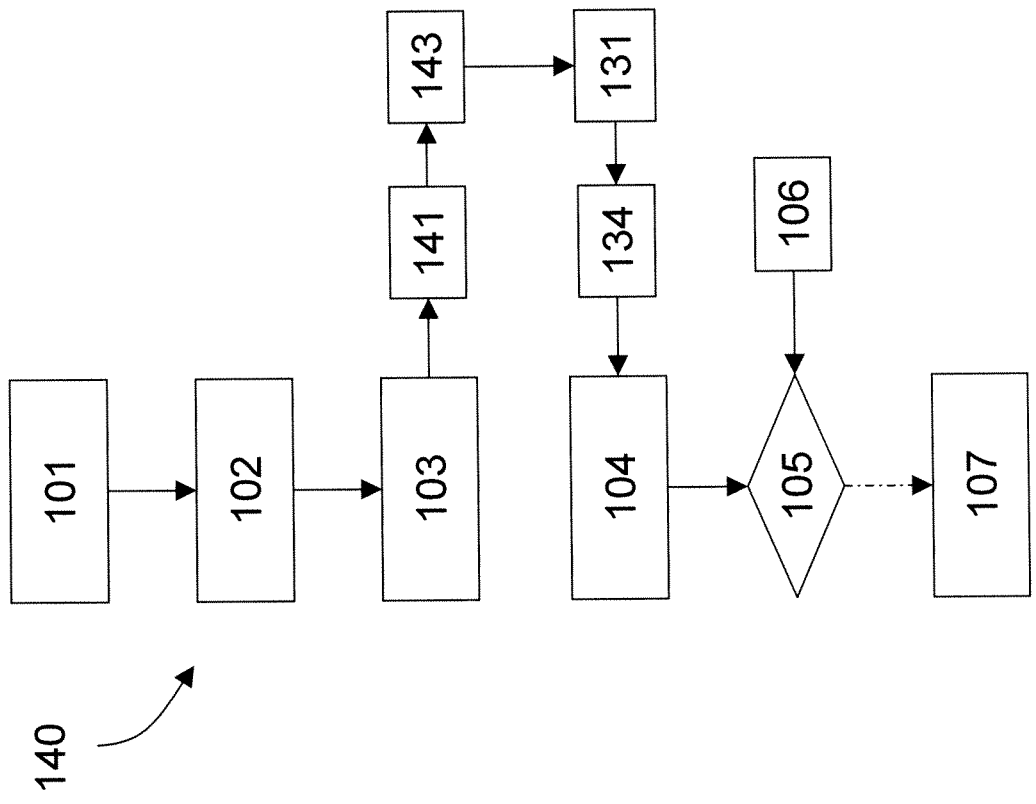

The second of said alternatives is realized in the method 140 shown in the FIG. 11, which additionally to the method steps 101 to 105 and 131 and 134 comprises the steps: 141 repeated detection of at least one changing measurement temperature from said at least first temperature measurement device, which is assigned to said first tempering device, at times after said second time, comparison of said changing measurement temperature with a comparison temperature; 143 detection of a time, at which said changing measurement temperature has reached said comparison temperature within the limits of a tolerance, and using said time as said third time. The time difference, determined in step 104 as testing quantity, can either be compared with a stored quantity (step 106) or with another testing quantity (step 106b).

Figure 12:
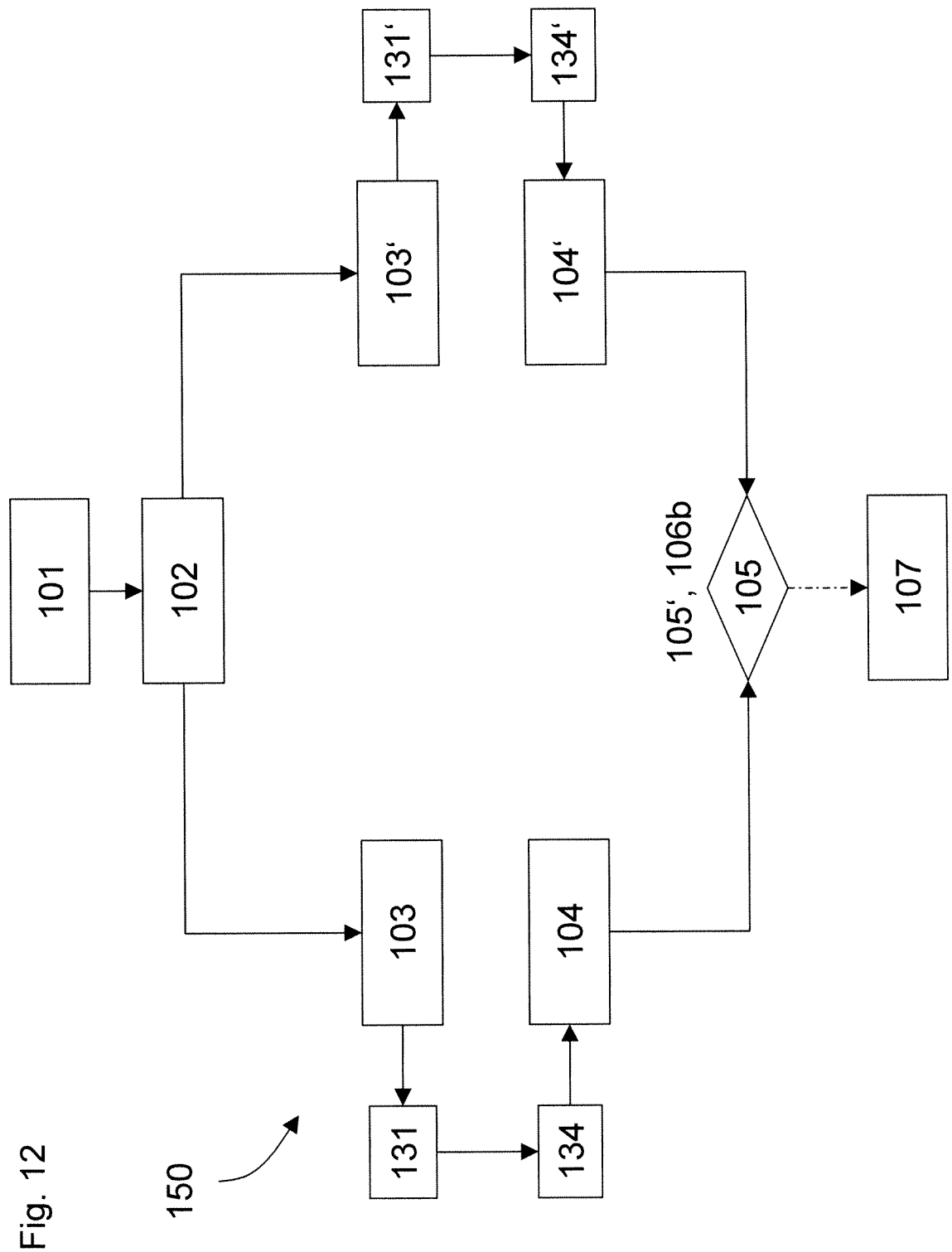

In FIG. 12 the method 150 is shown, at which two time differences are determined as testing quantities. It can, for example, be executed by a tempering apparatus, at which to one tempering device two temperature measurement devices are assigned to. Examples for such a tempering apparatus are the thermocyclers shown in FIGS. 1 and 2. The tempering device with its assigned first temperature measurement device forms a first component network and forms with its assigned second temperature measurement device a second component network, wherein for each network an own testing quantity for the characterization of the capability of the network is detected. The method 150 starts automatically (step 101) after the execution of a tempering program and tempers the tempering block with the tempering device from a first time (102). For the control loop of the tempering apparatus, to which the tempering device is assigned to, for example a set value is predefined. By means of the two temperature measurement devices, which are assigned to said tempering device, respectively two temperature values are determined at two times. The both times of the temperature measurements, namely firstly said second time and thereafter said third time are determined, before the set temperature is reached. The predefined constant temperature difference, upon whose expiration said third time is determined, amounts, for example, 30° C. The time difference between the third and second time, which is assigned to the first component network and which is determined as the first testing quantity, is, for example. 30 seconds, the second testing quantity, which is assigned to the second component network, is, for example, 35 seconds. Assumed, that the (reference-)value which is under the chosen conditions normally expected, for the time difference would be 30 seconds with a tolerance of 0.5 seconds. Then either both temperature sensors are defect or the tempering device is defect. It is less probable that two components at the same time show a malfunction than that only one component is malfunctioning. Therefore, in that case it is more probable that the tempering device provides a malfunction, for example a malfunctioning connection to the tempering block. In this way, by the configuration of the tempering apparatus using two sensors per control loop and tempering device as well as the method according to the invention, additional safety at the analysis of the operational status of the tempering apparatus can be gained.

FIG. 13 shows a method 160, at which two differently configured methods according to the invention are combined to one testing method, whereby a especially reliable testing of the operating condition of a tempering apparatus is achieved. The method 160 is for example executed by a tempering apparatus, at which to one tempering device two temperature measurement devices are assigned to, see FIGS. 1 and 2. One first testing quantity and one second testing quantity are determined in a temporally overlapping procedure. The method is started by a manual user input, which for example takes place via an input panel of the tempering apparatus, step 101. At the control loop of the tempering device a set value is applied (162) and the tempering device is caused to heat. The first testing quantity is a difference of two temperature values, which are detected by the temperature sensors, which are assigned to the tempering device, namely at said second time (103, 163) and whose difference is used as the first testing quantity (164, 104). To make sure that the temperature in the tempering block is finally adjusted at the positions of both temperature sensors, said second time is preferably chosen such that a delay time of for example 30 seconds after reaching of the temperature of the set value is included, during which the temperature stabilizes.

The second testing quantity in the method 160 is the period which is required for reaching of a predefined temperature difference. It corresponds thus to a temperature change velocity, without that however the quotient of temperature- and time difference is explicitly calculated. The period is determined by measuring not only at the times of said second time (103) of the method 160, but also additionally using two further times and two further temperature values. That times are a third time (131) and a further second time (103') wherein said third time is provided during the tempering, thus after said first time and after said further said second time. Said further second time (103') is preferably chosen such that the temperature set value has not yet reached such set temperature between the times provides and, for example, increasing profile, in particular a substantially ramp-shaped profile. The measured temperature difference can be delivered as well from said first or said second temperature sensor, or a combination of the sensors is used, for example by forming an average value.

The first testing quantity as well as the second testing quantity are compared with stored reference values (105, 106; 105", 106"), and respectively a partly result of the testing method is put out (107, 107"). With said combined, temporally overlapping method, further test data can be determined in a time saving manner, which give information about the operational status of the tempering apparatus. Preferably, such a combined testing method comprises further configurations of the method according to the invention, by for example after the determination of the first testing quantity, which was determined during the step of heating, determining further testing quantities, which are determined during cooling steps. For example, in said combined method sequentially the temperature values 35° C. (starting value), 95° C., 35° C., 95° C., 75° C., 55° C., 35° C. and 4° C. can be approached, and at each reaching of said set values a testing quantity can be determined. Thus, a testing method is created, which gives information on the operational capability of the tempering apparatus in different, operationally intended temperature regions and also on the heating performance as well as the cooling performance. Such a combined test method gives a especially complete information on the operating condition of the tempering apparatus.

The invention claimed is:

1. Tempering apparatus (1; 21; 31; 41; 61; 81) for the execution of a tempering program for at least one sample, comprising: at least one tempering block (4) configured for the reception of at least one sample, at least one tempering device (6; 38; 39; 48; 49; 86) arranged for the tempering of said at least one tempering block (4), at least one temperature measurement device assigned to said at least one tempering device, at least one control loop (9; 32; 42; 62; 82) for the regulation of a temperature, to which said at least one tempering device and said at least one temperature measurement device, which is assigned to said at least one tempering device, are assigned to, at least one control device (8; 58; 68; 88) configured for the control of the tempering of the at least one tempering block, characterized in that the tempering apparatus comprises at least two temperature measurement devices (7; 50; 51; 67; 87) assigned to at least one control loop, wherein said at least two temperature measurement devices serve as the measuring elements of the at least one control loop and comprise at least a first and a second temperature measurement device, and that to the tempering apparatus a at least one testing device (14; 24; 14'; 54; 74; 94) for the execution of a testing method is assigned to, wherein said testing device comprises a signal-connection (15; 17; 75; 95) to said at least first and second temperature measurement devices (7; 50; 51; 67; 87), such that by means of said signal-connection (15; 17; 75; 95) at least one testing quantity and a second testing quantity of the tempering apparatus are detectable, which characterizes the operational status of the tempering apparatus, wherein the tempering apparatus is configured for the execution of the testing method, which comprises the steps:

starting the method (101);

operation of at least said first tempering device for the duration of at least one first period from at least one first time (102);

detecting at least one measurement temperature from said at least one first temperature measurement device, which serves as a measuring element of the at least one control loop and which is assigned to said first tempering device, at least at a second time (103);

determining at least one first testing quantity of the tempering apparatus by using said at least one measurement temperature (104);

comparison of said first testing quantity with a reference quantity (105), wherein said reference quantity is said second testing quantity.

2. Tempering apparatus according to claim 1, characterized in that it comprises at least one control loop, to which at least two tempering devices and at least two temperature measurement devices are assigned to, wherein to each tempering device at least one temperature measurement device is assigned to.

3. Tempering apparatus according to claim 1, characterized in that it further comprises a starting device (18) for the starting of a testing method, wherein said starting device is in signal-connection with said testing device.

4. Tempering apparatus according to claim 3, characterized in that said starting device is configured for the manual starting of a testing method.

5. Tempering apparatus according to any one of claims 1-4, characterized in that it provides the function of a thermocycler, which is appropriate for the performance of a PCR-reaction in at least one PCR-sample.

* * * * *